US010920230B2

(12) United States Patent
Feinberg et al.

(10) Patent No.: US 10,920,230 B2
(45) Date of Patent: Feb. 16, 2021

(54) METHYLOTROPHS FOR AQUACULTURE AND ANIMAL FEED

(71) Applicant: KnipBio, Inc., Lowell, MA (US)

(72) Inventors: Larry F. Feinberg, Harvard, MA (US); Christopher J. Marx, Moscow, ID (US)

(73) Assignee: KnipBio, Inc., Lowell, MA (US)

( * ) Notice: Subject to any disclaimer, the term of this patent is extended or adjusted under 35 U.S.C. 154(b) by 1415 days.

(21) Appl. No.: 14/454,816

(22) Filed: Aug. 8, 2014

(65) Prior Publication Data

US 2015/0044327 A1    Feb. 12, 2015

Related U.S. Application Data

(60) Provisional application No. 61/863,701, filed on Aug. 8, 2013.

(51) Int. Cl.
  *A23K 50/80*    (2016.01)
  *A23L 5/44*    (2016.01)
  (Continued)

(52) U.S. Cl.
  CPC .............. *C12N 15/74* (2013.01); *A23K 10/12* (2016.05); *A23K 20/179* (2016.05); *A23K 50/80* (2016.05);
  (Continued)

(58) Field of Classification Search
  CPC .... A23K 20/179; A23K 50/80; A23K 1/1606; C12P 23/00; C12N 9/88; C12N 9/90; C12N 15/74; C12N 1/20; A23L 5/44
  See application file for complete search history.

(56) References Cited

U.S. PATENT DOCUMENTS

| | | | |
|---|---|---|---|
| 7,064,196 B2 | 6/2006 | Cheng et al. | |
| 2003/0003528 A1* | 1/2003 | Brzostowicz | C12N 9/88 |
| | | | 435/67 |

(Continued)

FOREIGN PATENT DOCUMENTS

| | | |
|---|---|---|
| WO | 02/18617 A2 | 3/2002 |
| WO | 2014/158590 A1 | 10/2014 |

OTHER PUBLICATIONS

Englund et al., "Production of isoprenoids in synechocystis PCC 6803" from 11th workshop of Cyanobacteria, Washington University in St. Louis, Aug. 7-11, 2013.*
Englund et. al., "PRoduction of Squalene in *Synechocystis* sp. PCC 6803". PLOS ONE, vol. 9, Issue 3 (Mar. 2014) (Year: 2014).*
Agashe et al,. "Good codons, bad transcript: large reductions in gene expression and fitness arising from synonymous mutations in a key enzyme." Mol. Biol. Evol. 30:549-560 (2013).

(Continued)

*Primary Examiner* — Erik Kashnikow
*Assistant Examiner* — Assaf Zilbering
(74) *Attorney, Agent, or Firm* — FisherBroyles, LLP; Jill A. Jacobson

(57) ABSTRACT

Disclosed are methods of producing carotenoid compounds in a methylotrophic bacterial host cell. Such a host cell may be an unmodified *Methylobacterium*, spontaneous mutant, or transformed cell, any of which exhibit favorable properties, such as overproduction of carotenoid compounds, increased carbon flux, improved growth, or the production of additional nutrients, such as protein, vitamins, antioxidants, or fatty acids. Also disclosed are feed compositions for use in aquaculture, or as animal feed, or as human nutritional supplements containing processed or unprocessed biomass from such cells, as are methods of preparation of the feed compositions.

22 Claims, 6 Drawing Sheets

Specification includes a Sequence Listing.

(51) Int. Cl.
| | |
|---|---|
| *A23K 10/12* | (2016.01) |
| *A23K 20/179* | (2016.01) |
| *C12N 1/20* | (2006.01) |
| *C12N 9/88* | (2006.01) |
| *C12N 9/90* | (2006.01) |
| *C12N 15/74* | (2006.01) |
| *C12P 23/00* | (2006.01) |

(52) U.S. Cl.
CPC .................. *A23L 5/44* (2016.08); *C12N 1/20* (2013.01); *C12N 9/88* (2013.01); *C12N 9/90* (2013.01); *C12P 23/00* (2013.01)

(56) References Cited

U.S. PATENT DOCUMENTS

| | | | |
|---|---|---|---|
| 2003/0182687 A1* | 9/2003 | Cheng | C12N 15/52 800/282 |
| 2004/0116514 A1 | 6/2004 | Nishino et al. | |
| 2004/0259959 A1 | 12/2004 | Sharoni et al. | |
| 2005/0124033 A1* | 6/2005 | Sharpe | C12N 9/0083 435/67 |
| 2007/0238149 A1 | 10/2007 | Cheng et al. | |
| 2008/0216756 A1* | 9/2008 | Horsfall | A23K 10/16 119/204 |
| 2012/0107360 A1 | 5/2012 | Le Butt et al. | |
| 2012/0156718 A1 | 6/2012 | Flachmann et al. | |
| 2012/0222148 A1 | 8/2012 | Turano et al. | |
| 2015/0191712 A1 | 7/2015 | Bott et al. | |
| 2015/0275241 A1 | 10/2015 | Herrema | |

OTHER PUBLICATIONS

Bertram et al., "Carotenoids and gene regulation" Nutr. Rev. 1999, 57(6):182-191.

Carroll et al., "Laboratory divergence of Methylobacterium extorquens AM1 through unintended domestication and past selection for antibiotic resistance" BMC Microbiology 14:2 (2014), 12 pages.

Chou, H.-H. et al. "Fast growth increases the selective advantage of a mutation arising recurrently during evolution under metal limitation." PLoS Genetics (2009) 5: e1000652, 12 pages.

Chou et al., "Diminishing returns epistasis among beneficial mutations decelerates adaptation" Science 332:1190-1192 (2011).

Chou and Marx, "Optimization of Gene Expression through Divergent Mutational Paths" Cell reports 1:1-8 (2012).

Chubiz et al., "A novel pair of inducible expression vectors for use in Methylobacterium extorquens" 2013. BMC Research Notes (6:183), 8 pages.

Delaney NF, Kaczmarek ME, Ward LM, Swanson PK, Lee M-C, et al. (2013) Development of an optimized medium, strain and high-throughput culturing methods for Methylobacterium extorquens. PLoS ONE 8: e62957. 10 pages. doi:10.1371/journal.pone.0062957.

Edge et al., "The carotenoids as anti-oxidants—a review." J. Photochem Photobiol B:Bio. 1997, 41:189-200.

Englund et al., Production of Squalene in *Synechocystis* sp. PCC 6803. PLoS ONE. 2014;9(3):8 pages.

International Search Report and Written Opinion for Application No. PCT/US2014/050282, dated Feb. 24, 2015 (16 pages).

Knief et al., Competitiveness of diverse methylobacterium strains in the phyllosphere of *Arabidopsis thaliana* and identification of representative models, including M. extorquens PA1. Microb Ecol. 60: 440-452, 2010. doi:10.1007/s00248-010-9725-3.

Koyama, Y., New trends in photobiology: Structures and functions of carotenoids in photosynthetic systems. Journal of Photochemistry and Photobiology B: Biology. Jun. 1991, vol. 9, issues 3-4, pp. 265-280.

Krinski, N.I., "The biological properties of carotenoids" Pure & Appl. Chem. 1994, 66(5):1003-1010.

Lee and Marx, "Synchronous waves of failed soft sweeps in the laboratory: remarkably rampant clonal interference of alleles at a single locus." Genetics 193:943-952 (2013).

Lee et al., "Asymmetric, bimodal trade-offs during adaptation of methylobacterium to distinct growth substrates" Evolution. (2009) 63(11): 2816-2830.

Marx, C. J. and Lidstrom, M. E. "Development of improved versatile broad-hostrange vectors for use in methylotrophs and other Gram-negative bacteria" Microbiology (2001) 147: 2065-2075.

Marx, C. J. and Lidstrom, M. E. "Broad-Host-Range cre-lox System for Antibiotic Marker Recycling in Gram-Negative Bacteria" BioTechniques (2002) 33: 1062-1067.

Marx et al., "Formaldehyde-detoxifying role of the tetrahydromethanopterin-linked pathway in Methylobacterium extorquens AM1." J. Bacteriol. 185: 7160-7165 (2003).

Marx, C. J. and M. E. Lidstrom "Development of an insertional expression vector system for Methylobacterium extorquens AM1 and generation of null mutants lacking mtdA and/or fch" Microbiology (2004) 150:9-19.

Marx CJ, Development of a broad-host-range sacB-based vector for unmarked allelic exchange. BMC Research Notes 1: 1 (2008), 8 pages. doi:10.1186/1756-0500-1-1.

Marx et al., "Complete genome sequences of six strains of the genus *Methylobacterium*" 2012. J. Bacteriology 194:4746-4748.

Michener et al, "Phylogeny poorly predicts the utility of a challenging horizontally transferred gene in Methylobacterium strains." 2014. J. Bacteriology. 196:2101-2107.

Scott, et al., "Sequences of versatile broad-host-range vectors of the RK2 family." Plasmid 50(1): 74-79 (2003).

Shahidi, F., et al., Carotenoid pigments in seafoods and aquaculture. Crit Rev Food Sci Nutr. Jan. 1998;38(1):1-67.

Van Dien et al., "Genetic characterization of the carotenoid biosynthetic pathway in Methylobacterium extorquens AM1 and isolation of a colorless mutant." 2003. Applied & Environmental Microbiology, vol. 69, issue 12, pp. 7563-7566.

Vuileumier et al., "Methylobacterium Genome Sequences: A Reference Blueprint to Investigate Microbial Metabolism of C1 Compounds from Natural and Industrial Sources" 2009. PLoS One, vol. 4, issue 5, e5584, 16 pages.

Welander, et al., Hopanoids play a role in membrane integrity and pH homeostasis in Rhodopseudomonas palustris TIE-1. J Bacterial. Oct. 2009;191(19):6145-56. doi: 10.1128/JB.00460-09. Epub Jul. 10, 2009.

European Office Action for Application No. EP 14806750.7, dated Feb. 23, 2017 (5 pages).

International Preliminary Report on Patentability for Application No. PCT/US2014/050282, dated Feb. 18, 2016 (9 pages).

Kalinowski, C. T. et al., "Effect of different carotenoid sources and their dietary levels on red porgy (*Pagrus pagrus*) growth and skin colour," Aquaculture, 2005, v. 244, pp. 223-231.

Britton, G., The biosynthesis of carotenoids: a progress report, 1991, Pure & App. Chem. 63(1):101-108.

Lee, M.-C., et al., Asymmetric, Bimodal Trade-Offs During Adaptation of Methylobacterium to Distinct Growth Substrates, 2009, Evolution 63-11:2816-2830.

Sharpe, P., et al., Use of Transposon Promoter-Probe Vectors in the Metabolic Engineering of the Obligate Methanotroph *Mehtylomonas* sp. Strain 16a for Enhanced C40 Carotenoid Synthesis, 2007, Applied and Environmental Microbiology 73(6):1721-1728.

Tang, X.-S., et al., Improvement of a CrtO-type of Beta-Carotene ketolase for canthaxantin production in *Methylomonas* sp., 2007, Metabolic Engineering 9:348-354.

Tao, L., et al., Expression of bacterial hemoglobin genes to improve astaxanthin production in a methanotrophic bacterium *Methylomonas* sp., 2007, Appl Microbiol Biotechnol 74:625-633.

Tlusty, M, et al., A transdisciplinary approach to the initial validation of a single cell protein as an alternative protein source for use in aquafeeds, 2017, PeerJ 5:e3170; DOI 10.7717/peerj.3170.

Ye., R., et al., Construction of the astaxanthin biosynthetic pathway in a methanotrophic bacterium *Methylomonas* sp. strain 16a, 2006, J INd Microbiol Biotechnol DOI 10.1007/s10295-006-0197-x.

Agnello, G., et al., Discovery of a Substrate Selectivity Motif in Amino Acid Decarboxylases Unveils a Taurine Biosynthesis Pathway in Prokaryotes, 2013, ACS Chemical Biology 8(10):1-17.

(56) References Cited

OTHER PUBLICATIONS

Abe, Y., et al., Role of the Osmolyte Taurine on the Folding of a Model Protein, Hen Egg White Lysozyme, Under a Crowding Condition, 2015, Amino Acids 47(5):1-7.
Korotkova, N., et al., Poly-Beta-Hydroxybutyrate Biosynthesis in the Facultative Methylotroph Methyloacterium extroquens AM1:Identificatin and Mutation of gap11, gap20, and phaR, 2002, Joural of Bacteriology 184, 6174-6181.
Sabirova, J., The 'LipoYeast' project: using the oleaginous yeast *Yarrowia lipolytica* in combination with specific bacterial genes for the bioconversion of lipids, fats and oils into high-value products, 2011, icrobiol Biotechnology 4:47-54.
Henke, N., et al., Production of the Marine Carotenoid Astaxanthin by Metabolically Engineered Corynebacterium glutamicum, 2016, Marine Drugs 14(7):124, 1-21.
Kwon, S., et al., Genomic Makeup of the Marine Flavobacterium Nonlabens (Donghaenana) dokdonensis and Identification of a Novel Class of Rhodopsins, 2013, Genome Biology and Evolution 5(1):187-199.
Alcaino, J., et al., Carotenoid Distribution in Nature, 2016, Subcellular Biochemistry 79:3-33.
Kim, S., et al., The astaxanthin dideoxyglucoside biosynthesis pathway in *Sphingomonas* sp., PB304, Applied Microbiology and Biotechnology, 2014, 98(24):9993-10003.
Liao, J.K., Squalene Synthase Inhibitor Lapaquistat Acetate. Could Anything Be Better Than Statins?, Circulation, 2011, 123:1925-1928.
Sivy, T.L., et al., Evidence of Isoprenoid Precursor Toxicity in Bacillus subtilis, Bioscience, Biotechnology, and Biochemistry, 2011, 75(12):2376-2383.

\* cited by examiner

Astaxanthin

β-Carotene

Canthaxanthin

β-Cryptoxanthin

Lutein

Zeaxanthin

Spirilloxanthin

SEQUENCE LISTING

<160> NUMBER OF SEQ ID NOS: 48

<210> SEQ ID NO 1
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tgacgtctag atctgaattc agctgtacaa ttggtaccat ggatgcatat ggcggccgca      60

<210> SEQ ID NO 2
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gactagtgag ctcaccggtt aacacgcgta cgtagggccc gcggtatcga taagctggat      60
cc                                                                    62

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cgggtttcgt gacctgttc                                                  19

<210> SEQ ID NO 4
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gttatgcggc cgccatctgc atggaagcca tccttgtttg c                         41

<210> SEQ ID NO 5
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gcttatcgat accgtcgacc tcgaggcagt cctgggcaga                           40

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cgggcatcga gcgtttcac                                                19

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ggtgacggca ttgaagctg                                                19

<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
catgcatctt tggtcttcat cgtgaatg                                       28

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
accgcggtcg tgctgtacta atcc                                           24

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
agagctcgat accgaccgat agatctc                                        27

<210> SEQ ID NO 11
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
caacaactta taccatggcc tacaaaaagg caaacaatgg tacttgacga ctcatcacaa    60

<210> SEQ ID NO 12
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12

```
gtccgttcgt tacaatctac aactacaatt gttgtgatga gtcgtcaagt accattg         57

<210> SEQ ID NO 13
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
atagggcccc aacaacttat accatggcct ac                                    32

<210> SEQ ID NO 14
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ataggtaccg tccgttcgtt acaatctaca ac                                    32

<210> SEQ ID NO 15
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
atacgtctca tccctatcag tgatagagag ttgtagattg taacgaacgg ac              52

<210> SEQ ID NO 16
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
atacgtctca gggacgtcaa gtaccattgt ttgcc                                 35

<210> SEQ ID NO 17
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
atacgtctca acaaacagac aatctggtct gtttgtggta cccaattcgc cctag           55

<210> SEQ ID NO 18
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
atacgtctca ttgtttacaa tctacaacta caattgttgt g                          41
```

<210> SEQ ID NO 19
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
atagctagca gggagagacc ccgaatgatg tctagattag ataaaagtaa agtg         54

<210> SEQ ID NO 20
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
atagggccct taagacccac tttcacattt aag                                33

<210> SEQ ID NO 21
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
acgcgaaatt caagcgctag ggccaagttg ggtaacgcca gggttttccc              50

<210> SEQ ID NO 22
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
atgtgaaagt gggtcttaag ggccaagttg g                                  31

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gtaacgccag ggttttccc                                                19

<210> SEQ ID NO 24
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tgtaggccat ggtataagtt gttgggatgc aaaaacgagg ctagtttacc              50

<210> SEQ ID NO 25
<211> LENGTH: 61
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 25
gataggtacc tctagaagat ctacgcgtac tagtgcatgc gagctcaccg gtgattcata    60
g    61

<210> SEQ ID NO 26
<211> LENGTH: 61
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 26
ctatgaattc accggtgagc tcgcatgcac tagtacgcgt agatcttcta gaggacctat    60
c    61

<210> SEQ ID NO 27
<211> LENGTH: 48
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 27
atggatgcat atgctgcagc tcgagcggcc gcggcccct ttgcccctt    48

<210> SEQ ID NO 28
<211> LENGTH: 29
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 28
atccggcacg gttgacacta tggctggga    29

<210> SEQ ID NO 29
<211> LENGTH: 48
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 29
gcgctgacga aaatcccagc catagtgtca accgtgccgg atgcccgt    48

<210> SEQ ID NO 30
<211> LENGTH: 48
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 30
ggttaacacg cgtacgtagg gcccgcggcc gcgggcgatg ttggtgaa                48

<210> SEQ ID NO 31
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
atggatgcat atgctgcagc tcgagcggcc gcccgattgc ctgcccctag              50

<210> SEQ ID NO 32
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ggatcaacgg tgatgcgagg cggagcgcat tttcggtggc aggcgcctga gcgaagtcc   59

<210> SEQ ID NO 33
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ctgccaccga aaatg                                                    15

<210> SEQ ID NO 34
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ttagcgccgc ggcaaggccg gttct                                         25

<210> SEQ ID NO 35
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
cgagcgatgg cgtgagaacc ggccttgccg cggcgctaag agtgt                   45

<210> SEQ ID NO 36
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36

```
ggttaacacg cgtacgtagg gcccgcggcc gccgaatcgc cgctgaca          48
```

<210> SEQ ID NO 37
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37

```
ctccccatcc tcgtgatc                                           18
```

<210> SEQ ID NO 38
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38

```
gaggaaggcg tccgggtc                                           18
```

<210> SEQ ID NO 39
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39

```
gtgccggatg cccg                                               14
```

<210> SEQ ID NO 40
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40

```
cgccgaaacc cggatg                                             16
```

<210> SEQ ID NO 41
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41

```
gctcgccacc aagttcg                                            17
```

<210> SEQ ID NO 42
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42

```
cgccgaaacc cggatg                                             16
```

<210> SEQ ID NO 43
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
taccatggat gcatatgctg cagctcgagc ccgcgccgca ggaattc                47

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
cgcatcgttc tcgcctcgtt c                                            21

<210> SEQ ID NO 45
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
gagacagtcg aacgaggcga gaacgatgcg gcaacctgaa gcggggcaac             50

<210> SEQ ID NO 46
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ggttaacacg cgtacgtagg gcccgcggcc gattgagacc cgcgggtcat c           51

<210> SEQ ID NO 47
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
tatgctgcag ctcgagcggc cgc                                          23

<210> SEQ ID NO 48
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
ggccgctcga gctgcagca                                               19

METHYLOTROPHS FOR AQUACULTURE AND ANIMAL FEED

PRIORITY

This application claims priority to U.S. provisional patent application No. 61/863,701, filed on Aug. 8, 2013, which is incorporated herein by reference in its entirety.

SEQUENCE LISTING

The instant application contains a Sequence Listing which has been submitted electronically in ASCII format and is hereby incorporated by reference in its entirety. Said ASCII copy, created on Aug. 7, 2014, is named 0114922-00002 SL.txt and is 11,507 bytes in size.

BACKGROUND

Carotenoids are a class of ubiquitous and structurally diverse natural pigments ranging in color from light yellow to orange to red. Carotenoids are responsible for the coloring of carrots, tomatoes, red peppers, and the petals of daffodils and marigolds, as well as lobsters, salmon, and other marine life. Carotenoids are produced by all photosynthetic organisms, as well as by some bacteria and fungi. Carotenoids have roles in photosynthesis, nutrition, and protecting against photooxidative damage. Animals cannot produce carotenoids themselves, but must obtain these nutritionally important compounds through their diet. Carotenoids are 40-carbon ($C_{40}$) terpenoids ultimately derived from the isoprene biosynthetic pathway, specifically from isopentenyl pyrophosphate (IPP), a five-carbon building block. This biosynthetic pathway can be divided into two portions: the upper isoprene pathway, which leads to the formation of IPP, and the lower carotenoid biosynthetic pathway, responsible for converting IPP into long chain (e.g., $C_{30}$ and $C_{40}$) carotenogenic compounds.

Carotenoid compounds, such as β-carotene, astaxanthin, and spirilloxanthin, are used industrially as ingredients for food and feed stocks, both serving a nutritional role and often increasing desirability of the product to consumers. Carotenoids, such as astaxanthin and canthaxanthin, are often added to aquaculture feeds for the purpose of adding color to the flesh of aquacultured organisms; their wild counterparts have colored flesh resulting from consumption of carotenoids that occur naturally in Crustacea or algae, or in other fish that have consumed algae. For example, astaxanthin is widely used in salmon aquaculture to produce the orange coloration found in wild salmon. Some carotenoids are also precursors of vitamin A. Moreover, some carotenoids have antioxidant properties, and may have health benefits (see, for example, Jyonouchi et al., *Nutr. Cancer* 16:93, 1991; Giovannucci et al., *J. Natl. Cancer Inst.* 87:1767, 1995; Miki, *Pure Appl. Chem.* 63:141, 1991; Chew et al., *Anticancer Res.* 19:1849, 1999; Wang et al., *Antimicrob. Agents Chemother.* 44:2452, 2000). Several carotenoids (e.g., β-carotene, lycopene, and lutein) are currently sold as nutritional supplements.

A number of carotenoids have been produced in microbial organisms. For example, Intl Pat. Appl.Pub. No. WO 02/18617 describes a method of production of carotenoid compounds using microorganisms that metabolize single carbon substrates. Genes encoding elements of the carotenoid biosynthetic pathway have been cloned and expressed in fungi, yeast, and microbes. For example, lycopene has been produced from genetically engineered *E. coli* and *Candida utilis* (Farmer, W. R. et al. (2001) *Biotechnol. Prog.* 17: 57-61; Wang, C. et al., (2000) *Biotechnol Prog.* 16: 922-926; Misawa, N. and H. Shimada (1998) *J. Biotechnol.* 59: 169-181; Shimada, H. et al. (1998) *Appl. Environm. Microbiol.* 64: 2676-2680). Zeaxanthin has been produced from recombinant *E. coli* and *Candida utilis* (Albrecht, M. et al., (1999). *Biotechnol. Lett.* 21: 791-795; Miura, Y. et al. (1998) *Appl. Environm. Microbiol.* 64: 1226-1229). Astaxanthin has been produced from *E. coli* and *Pfaffia rhodozyma* (see, for example, U.S. Pat. No. 5,466,599 (incorporated by reference)). The nutrient β-carotene has been produced from *E. coli, Candida utilis* and *Pfaffia rhodozyma* (Albrecht, M. et al. (1999) *Biotechnol. Lett.* 21: 791-795; Miura, Y. et al. (1998) *Appl. Environm. Microbiol.* 64: 1226-1229; U.S. Pat. No. 5,691,190 (incorporated by reference)).

Genes encoding geranylgeranyl pyrophosphate synthase, lycopene cyclase, and phytoene dehydrogenase from *Erwinia herbicola* have been expressed in *E. coli* (see, for example, U.S. Pat. Nos. 5,545,816; 5,656,472; 5,530,189; and 5,530,188, all of which are incorporated by reference). Genes encoding such carotenoid products as geranylgeranyl pyrophosphate, phytoene, lycopene, β-carotene, and zeaxanthin-diglucoside, from *Erwinia uredovora* have been expressed in *E. coli, Zymomonas mobilis*, and *Saccharomyces cerevisiae* (U.S. Pat. No. 5,429,939). Carotenoid biosynthetic genes including crtE, crtB, crtl, crtY, and crtZ taken from *Flavobacterium* have been recombinantly expressed (see U.S. Pat. No. 6,124,113).

Although the above methods can produce useful amounts of carotenoids, a need exists for improved methods. A particular long-appreciated need is for a process that produces useful yields of carotenoids from an inexpensive feedstock and also produces one or more nutrients (e.g., lipids or protein). The resulting carotenoid- and nutrient-rich microbial or plant biomass could then be processed into feed for aquaculture or agriculture, or used as a nutrient source for humans.

There are a number of microorganisms that utilize single-carbon substrates as their sole energy sources. Examples of single-carbon substrates include methane, methanol, formate, thiols, and methylated amines. These organisms are referred to as methylotrophs and also herein as "C1 metabolizers". Few methylotrophs have been successfully utilized to produce nutrients on an industrial scale. Despite the fact that single-carbon substrates are cost-effective energy sources, the lack of information about methylotroph genetics and the resulting difficulty in manipulation has limited their use primarily to the synthesis of native products.

A need also exists for low-cost, complete nutrition for use in aquaculture. Aquaculture is the propagation, cultivation and marketing of aquatic animals and plants in a controlled environment. The aquaculture industry is currently the fastest growing food production sector in the world. World aquaculture produces approximately 60 million tons of seafood at an annual value of more than $70 billion (USD). Presently, fish farming produces about half of all fish consumed globally and this percentage is growing as a result of declining yields from wild-caught fish in both marine and freshwater environments. Species groups produced in aquaculture include: carps and other cyprinids; oysters; clams, cockles and arkshells; scallops; shrimps and prawns; salmons, trouts and smelts; mussels; and tilapias and other cichlids.

While certain species (e.g., tilapia) can be fed an exclusively vegetarian diet, others require a carnivorous diet. Feed for carnivorous fish typically comprises fishmeal and fish oil derived from wild caught species of small pelagic fish (predominantly anchovy, jack mackerel, blue whiting, capelin, sandeel and menhaden). The fishmeal and/or fish oil are processed into a pelleted or flaked feed, depending on the size of the fish to which it will be fed (e.g., fry, juveniles, adults). Other components of the aquaculture feed composition may include pigments, vegetable protein, vitamins, and minerals.

Fish oils from ocean-caught fish have traditionally been used as the sole dietary lipid source in commercial fish feed because of abundant supply, low cost, and high percentage of essential fatty acids. These "essential fatty acids" are required for normal growth, health, reproduction, and other functions. In fact, all vertebrate species, including fish, have a dietary requirement for both omega-6 and omega-3 polyunsaturated fatty acids ("PUFAs"). Eicosapentaenoic acid, or "EPA" (cis-5,8,11,14,17-eicosapentaenoic acid) is an omega-3 and docosahexaenoic acid, or "DHA" (cis-4,7,10,13,16,19-docosahexaenoic acid, a 22:6 omega-3) are two essential PUFAs.

About 87% of the global supply of fish oil is consumed for fish feed as a lipid source. Given that fish oil production has peaked at 1.5 million tons per year, the rapidly growing aquaculture industry will soon outpace the finite stocks of marine pelagic fish as a supply of fish oil. Therefore, it is essential to find and implement sustainable alternatives to fish oil that can keep pace with the ever growing global demand for fish products.

Many organizations recognize the limitations noted above with respect to fish oil availability and aquaculture sustainability. The National Oceanic and Atmospheric Administration and the Department of Agriculture (United States) have collaborated in an Alternative Feeds Initiative to " . . . identify alternative dietary ingredients that will reduce the amount of fishmeal and fish oil contained in aquaculture feeds while maintaining the important human health benefits of farmed seafood."

U.S. Pat. Appl. Pub. No. 2007/0226814 (incorporated by reference) discloses fish food containing at least one biomass obtained from fermenting microorganisms wherein the biomass contains at least 20% DHA relative to the total fatty acid content. Microorganisms from the genus *Stramenopiles* are mentioned as sources of DHA.

U.S. Pat. Appl. Pub. No. 2009/0202672 (incorporated by reference) discloses that stearidonic acid ("SDA"; 18:4 omega-3) can be added to aquaculture feed. This fatty acid can be obtained from a transgenic plant. Unfortunately, SDA is not converted efficiently to DHA in fish.

U.S. Pat. No. 7,932,077 (incorporated by reference) discloses that recombinantly engineered *Yarrowia lipolytica* may be a useful addition to most animal feeds, including aquaculture feeds, because it provides necessary omega-3 and/or omega-6 PUFAs, and based on its unique protein:lipid:carbohydrate composition, as well as unique complex carbohydrate profile (comprising an approximate 1:4:4.6 ratio of mannan:beta-glucans:chitin).

If the growing aquaculture industry is to sustain and even increase its contribution to world fish supplies, there is a need for alternative aquaculture feed compositions that: (i) reduce wild fish inputs by replacing fish oil and fish meal with non-fish derived sources; and (ii) use pigments that are not chemically synthesized, or otherwise derived from petroleum-based feedstocks, to provide pigmentation.

SUMMARY OF THE INVENTION

In certain embodiments, the present invention provides a biomass containing substantially one or more isolated methylotrophic bacterial cultures that are genetically modified or artificially pre-selected to produce elevated levels of a carotenoid compound relative to the corresponding unmodified or unselected bacterium. The carotenoid compound is, for example, β-carotene, lycopene, rhodopin, astaxanthin or spirilloxanthin. In certain embodiments, the bacterium is genetically modified so that one or more genes producing enzymes that divert isoprenoid compounds from the carotenoid biosynthetic pathway are blocked or deleted. In certain embodiments, the invention provides a bacterium that contains a non-lethal knock-out of shc, for example, *M. extorquens* comprising a non-lethal knock-out of shc. In other embodiments, the bacterium is selected by directed evolution as a spontaneous mutant that expresses a "dark pink" or "reddish" pigment.

In certain embodiments, the biomass can be in a dry, or substantially dry, form, e.g., containing less than 20%, 10%, 5%, 2% of moisture. In certain embodiments, the cultures are isolated by removing substantially all supernatant, such as by filtering, sedimentation, or centrifugation. In certain embodiments, the collection of cultures into the biomass and further processing of biomass excludes bacterial lysis step, e.g., by use of detergents or ultrasound. In certain embodiments, the processed bacterial cells maintain substantially whole cell membranes. In some embodiments, a substantial portion (e.g., more than 80%, 50%, 30%, 20%, 10% or 5%) of bacterial cells may maintain viability in the processed biomass.

The biomass of the invention may contain bacterial cultures selected from the group consisting of *Methylomonas*, *Methylobacter*, *Methylococcus*, *Methylosinus*, *Methylocyctis*, *Methylomicrobium*, *Methanomonas*, *Methylophilus*, *Methylobacillus*, *Methylobacterium*, *Hyphomicrobium*, *Xanthobacter*, *Bacillus*, *Paracoccus*, *Nocardia*, *Arthrobacter*, *Rhodopseudomonas*, *Pseudomonas*, *Candida*, *Hansenula*, *Pichia*, *Torulopsis*, and *Rhodotorula*. In certain preferred embodiments, the bacterium is *M. extorquens*. In further embodiments, the strain of *M. extorquens* is selected from the group consisting of *M. extorquens* AM1, *M. extorquens* DM4, *M. extorquens* CM4, *M. extorquens* PA1, *M. extorquens* BJ001 (formerly *M. populi*), *M. radiotolerans*, *M. nodulans*, and *Methylobacterium* spp. 4-46.

In a further aspect, the invention provides a feed composition, comprising the biomass. The feed composition may contain at least 1% of the biomass by weight. In certain embodiments, the feed composition is optimized for consumption by fish, seafood, humans, or other animals. For example, the feed may comprise one or more of EPA, DHA, taurine, and one or more essential amino acids.

In yet another aspect, the invention provides a method of producing fish or seafood, comprising: farming fish or seafood, and providing a diet, which includes the feed of the invention, to the fish or seafood. With respect to aquaculture, the feed may be particularly useful for species (farmed for human consumption) that has pink-, reddish-, yellow- or orange-colored flesh. One advantage is that the farming of fish may then fully exclude, or reduce the amount of, purified caratenoids used for supplementing the fish/seafood diet for esthetic purposes, thus substantially reducing the costs. Accordingly, the invention also provides a fish or seafood product exhibiting an elevated level of a carotenoid pigment in the flesh, wherein such elevated level is attributable to the diet comprising the feed composition of the invention. In certain embodiments, the fish meat contains at a higher level of at least one carotenoid compound than substantially same fish on a regular diet. Such a level may be higher by at least 10%, 15%, 20%, 25%, 50%, 80%, 100%, 200%, 300%, 400%, 500%, 1000% or more. In appearance, such a product would have a visibly darker, more appealing pigmentation. In related further embodiments, such food product is also characterized in that it does not contain, or contains less of, artificially introduced antibiotics or anti-inflammatory compounds, due to a healthier diet consumed by fish or seafood.

DETAILED DESCRIPTION

Introduction

Figure 1:
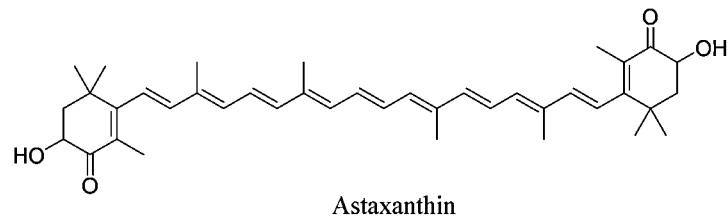
FIG. 1 shows several exemplary carotenoid compounds.
Figure 1:
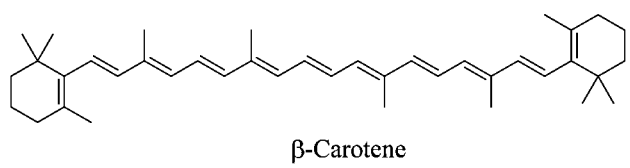
Figure 1:
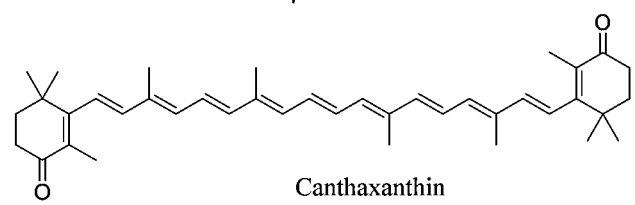
Figure 1:
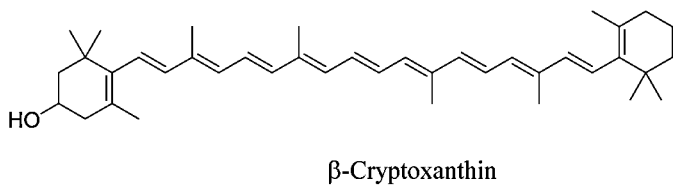
Figure 1:
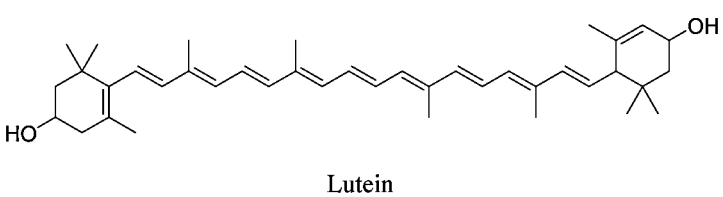
Figure 1:
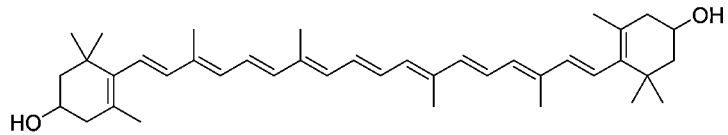
Figure 1:
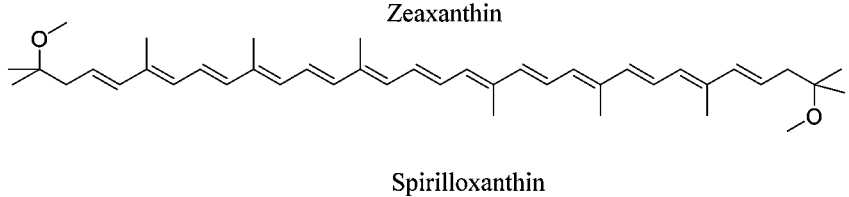

This invention provides, in one aspect, pigmented methylotrophic organisms (e.g., *Methylobacterium*) capable of producing one or more carotenoids. In certain embodiments, such organisms use methanol, methane, or another C1 energy source. In certain embodiments, such C1 energy source is the sole energy source for the organism. In certain embodiments, the methylotroph is *M. extorquens*. In certain embodiments, the *M. extorquens* or other methylotroph exhibits improved properties, such as improved yield of one or more carotenoids, production of a desired carotenoid spectrum, improved carotenoid levels per unit of biomass or as measured by a percentage of dry cell weight. In certain embodiments, the *M. extorquens* or other methylotroph is capable of producing specific desired nutrients, such as one or more proteins, one or more lipids, carbohydrates, and one or more vitamins. In certain embodiments, the protein produced is a complete nutrient source for aquaculture, agriculture, or humans.

The present invention also provides methods of engineering and culturing such methylotrophs, methods of using such methylotrophs to produce carotenoids, and methods of preparing carotenoid-containing compositions, such as food or feed additives, or nutritional supplements, using carotenoids produced in such methylotrophs. In particular, the present invention provides systems and methods for generating methylotrophs containing one or more oleaginic, proteinogenic and/or carotenogenic modifications that increase or alter their lipid-, protein-, or carotenoid-producing capabilities as compared with otherwise identical organisms that lack the modification(s). One preferred embodiment relates to an organism that produces one or more or all of the essential amino acids, for example lysine, valine, threonine, methionine, arginine, and taurine.

One aspect of this invention pertains to the field of aquaculture. More specifically, this invention pertains to aquaculture feed compositions comprising carotenoid-containing microbial biomass and a complete protein nutrition, that is, containing most or all amino acids necessary for healthy growth of the animal to which it is administered. The feed compositions may optionally contain omega-3 polyunsaturated fatty acid ratios of eicosapentaenoic acid to docosahexaenoic acid that are higher than currently available using fish oil, as well as further vitamins or other nutrients.

Detailed Description

One common class of single carbon metabolizers is the methanotrophs, which are characterized by their ability to use methane as a sole source of carbon and energy. Methane monooxygenase is the enzyme required for the key step of methane metabolism. Its product is methanol (see Murrell et al., *Arch. Microbiol.* (2000), 173(5-6), 325-332). This reaction occurs at ambient temperature and pressures in sharp contrast to the industrial transformation of methane to methanol, which requires high temperatures (several hundred degrees Celsius) and high pressure (see WO 2000/007718 (incorporated by reference) and U.S. Pat. No. 5,750,821 (incorporated by reference)). This remarkable ability to transform methane under ambient conditions, along with the abundance of methane, makes the biotransformation of methane a potentially valuable process. No less desirable are methylotrophs capable of metabolizing methanol, which is itself an abundant and cheap feedstock. Being a liquid at room temperature, methanol is more easily utilized than methane for many applications.

The ketocarotenoid astaxanthin (3,3-dihydroxy-β,β-carotene-4,4'-dione) was first conceptualized as an oxidized form of β-carotene. Astaxanthin was subsequently found to be ubiquitous across many types of marine animals and algae. Few animals have the biosynthetic machinery to produce astaxanthin; most of them obtain it from their food. Astaxanthin is found in the plant kingdom principally in some species of cyanobacteria, algae and lichens.

Astaxanthin is a powerful antioxidant, being an inhibitor of lipid peroxidation (see, for example, Kurashige, M. et al. (1990) *Physiol. Chem. Phys. Med. NMR* 22:27). Also attributed to astaxanthin are chemopreventive effects such as significantly reducing the incidence of induced murine urinary bladder cancer (see Tanaka, T. et al. (1994) *Carcinogenesis* 15:15). Astaxanthin also exerts immunomodulating effects, inter alia enhancing antibody production (see Jyonouchi, H. (1993) *Nutr. Cancer* 19:269). The current, albeit incomplete, picture is that it appears to play an important role in cancer and tumor inhibition, as well as eliciting a positive response from the immune system.

Many methylotrophs contain an inherent isoprenoid pathway that enables them to synthesize other non-endogenous isoprenoid compounds. Some organisms are known to possess carotenogenic biosynthetic genes and the upper isoprene pathway which produces carotenogenic precursor molecules. Certain aspects of the isoprenoid biosynthesis pathway are conserved throughout the fungal, bacterial, plant and animal kingdoms. These include proteins or homologs corresponding to acetoacetyl-CoA thiolase, HMG-CoA synthase, HMG-CoA reductase, mevalonate kinase, phosphomevalonate kinase, mevalonate pyrophosphate decarboxylase, IPP isomerase, FPP synthase, and GGPP synthase. An alternative isoprenoid biosynthesis pathway, sometimes called the "mevalonate-independent pathway", is utilized by some organisms (particularly bacteria). This pathway is initiated by the synthesis of DOXP (1-deoxy-D-xyloglucose-5-phosphate) from pyruvate and glyceraldehyde-3-phosphate. DOXP is then converted, via a series of biosynthetic steps, into IPP, which isomerizes into DMAPP and is then converted, via GPP and FPP, into GGPP.

Despite this knowledge, there is little precedent for genetically engineered C1 metabolizers producing specific, commercially valuable carotenoids. It is likely that the usefulness of these organisms for production of a larger range of chemicals is constrained by limitations including the relatively slow growth rates of methanotrophs, limited ability to tolerate methanol as an alternative substrate to methane, difficulty in genetic engineering, poor understanding of the roles of multiple carbon assimilation pathways present in methanotrophs, and potentially high costs due to the oxygen demand of fully saturated substrates such as methane. The problem to be solved is how to provide a cost effective method for the microbial production of carotenoid compounds, using organisms which utilize C1 compounds as their carbon and energy source.

Salmon and shrimp aquaculture would benefit from application of the present invention because of the importance of carotenoid pigmentation to the value of these organisms. (see Shahidi, F. et al. *Science* (1998) 38(1): 1-67). Lastly, carotenoids find applications in the synthesis of steroids, fragranaces, flavors, and compounds with electronics applications. Astaxanthin is the most expensive commercially used carotenoid compound, priced at thousands of dollars per kilogram. The disclosure herein provides a detailed description of the selection, modification, and use of appropriate C1 metabolizing microorganisms for the high-yielding production of various carotenoid compounds.

According to the present invention, carotenoid production in a host organism may also be accomplished through modifying the expression or regulating the activity of one or more proteins involved in isoprenoid biosynthesis. In certain embodiments the modification comprises removing alternative pathways that draw off intermediates at various stages. Genes encoding these enzymes can be cleanly removed using a marker-free allelic exchange system such as one based upon cre-lox (Marx, C. J. and Lidstrom, M. E. *BioTechniques* (2002) 33: 1062-1067), or a two-step, "in-out" system such as one based upon negative selection of sacB-containing strains (Marx, C. J. *BMC Research Notes* (2008) 1:1). Many of these genes are commonly clustered on the chromosome, thereby facilitating their removal. For example, one may remove one or more genes for enzymes or the enzymes themselves that make squalene and hopene on the route to hopanoid biosynthesis. Such genes and enzymes include squalene synthase, encoded by hpnC, dehydrosqualene synthase, encoded by hpnD, dehydrosqualene reductase, encoded by hpnE, or squalene-hopene synthase, encoded by she (also known as hpnF) (Bradley, A. S. et al. *Organic Geochemistry* (2010) 41: 1075-1081). Another offshoot that can be removed is the addition of a reduced geranylgeranyl group as an ester to bacteriochlorophyll (Addlesee, H. A. and Hunter, C. N. *Journal of Bacteriology* (1999) 181: 7248-7255). These reactions are accomplished by geranylgeranyl bacteriochlorophyll synthase, encoded by bchG, and geranylgeranyl-bacteriochlorophyll reductase, encoded by bchP. Finally, rather than synthesizing spirilloxanthin, for another product like astaxanthin it will be advantageous to remove enzymes downstream of where these pathways diverge. In this case, enzymes downstream of lycopene should be removed. These consist of hydroxyneurosporene dehydrogenase, encoded by crtC, methoxyneurosporene dehydrogenase, encoded by crtD, and hydroxyneurosporene methyltransferase, encoded by crtF. In certain embodiments, it will be advantageous to increase expression of endogenous genes upstream of lycopene. These include 1-deoxy-D-xylulose-5-phosphate synthase, encoded by dxs, 1-deoxy-D-xylulose-5-phosphate reductoisomerase, encoded by dxr, isopentyl diphosphate isomerase, encoded by idi, farnesyl diphosphate synthase, encoded by ispA, geranylgeranyl diphosphate synthase, encoded by crtE, phytoene synthase, encoded by crtB, and phytoene desaturase, encoded by crtI. In certain embodiments, such modification comprises heterologous expression of isoprenoid biosynthesis polypeptides in the host organism and/or modifications of the expression or modifying the activity of one or more endogenous or heterologous isoprenoid biosynthesis polypeptides. Preferred carotenoids include astaxanthin and spirilloxanthin. In view of the considerable conservation of components of the isoprenoid biosynthesis polypeptides, one would expect that heterologous isoprenoid biosynthesis proteins would function even in significantly divergent organisms. In order to optimize expression in the methylotrophic host, such as *M. extorquens*, the sequence may be codon-optimized to match the most frequently used codons in the host organism. Indeed, in many cases proteins from different source organisms will function together (i.e., at the same time). In certain embodiments of the invention, a plurality of different heterologous isoprenoid biosynthesis polypeptides is introduced into the host cell. In certain embodiments, this plurality contains only proteins from the same source organism (e.g., two or more sequences of, or sequences derived from, the same organism); in other embodiments the plurality includes polypeptides independently selected from different source organisms (e.g., two or more sequences of, or sequences derived from, at least two different organisms). In certain embodiments, astaxanthin production will be accomplished by introducing lycopene cyclase, encoded by crtY, β-carotene ketolase, encoded by crtW, and β-carotene hydroxylase, encoded by crtZ. It is anticipated that the desired production will be supplied by the introduction of CrtY (lycopene cyclase) from *Bradyrhizobium* sp. ORS 278 [GenBank sequence ID: YP_001208335.1] or the like; CrtW (beta-carotene ketolase) from *Bradyrhizobium* sp. ORS 278 [GenBank sequence ID: YP_001208332.1] or the like; and CrtZ (β-carotene hydroxylase) from *Brevundimonas* sp. SD212 [GenBank sequence ID: AB181388] or the like.

In certain embodiments, it may be useful to change the levels of macromolecules within cellular material in order to provide beneficial properties to the feed. This may include changing or altering components, such as exopolysaccharides, poly-β-hydroxybutyrate storage polymer, or cellulose. These modifications may divert more carbon flux toward other products, such as carotenoids, lipids, total protein, or engineered production of amino acids or vitamins.

In certain embodiments, genetic modifications will take advantage of freely replicating plasmid vectors for cloning. These may include small IncP vectors developed for use in *Methylobacterium*. These vectors may include pCM62, pCM66, or pHC41 for cloning (Marx, C. J. and M. E. Lidstrom *Microbiology* (2001) 147: 2065-2075; Chou, H.-H. et al. *PLoS Genetics* (2009) 5: e1000652).

In certain embodiments, genetic modifications will take advantage of freely replicating expression plasmids such as pCM80, pCM160, pHC90, or pHC91 (Marx, C. J. and M. E. Lidstrom *Microbiology* (2001) 147: 2065-2075; Chou, H.-H. et al. *PLoS Genetics* (2009) 5: e1000652).

In certain embodiments, genetic modifications will utilize freely replicating expression plasmids that have the ability to respond to levels of inducing molecules such as cumate or anhydrotetracycline. These include pHC115, pLC 290, pLC291 (Chou, H.-H. et al. *PLoS Genetics* (2009) 5: e1000652; Chubiz, L. M. et al. *BMC Research Notes* (2013) 6: 183).

In certain embodiments, genetic modifications will utilize recyclable antibiotic marker systems such as the cre-lox system. This may include use of the pCM157, pCM158, pCM184, pCM351 series of plasmids developed for use in *M. extorquens* (Marx, C. J. and M. E. Lidstrom *BioTechniques* (2002) 33: 1062-1067).

In certain embodiments, genetic modifications will utilize transposon mutagenesis. This may include mini-Tn5 delivery systems such as pCM639 (D'Argenio, D. A. et al. *Journal of Bacteriology* (2001) 183: 1466-1471) demonstrated in *M. extorquens* (Marx, C. J. et al. *Journal of Bacteriology* (2003) 185: 669-673).

In certain embodiments, genetic modifications will utilize expression systems introduced directly into a chromosomal locus. This may include pCM168, pCM172, and pHC01 plasmids developed for *M. extorquens* AM1 (Marx, C. J. and M. E. Lidstrom *Microbiology* (2001) 147: 2065-2075; Lee, M.-C. et al. *Evolution* (2009) 63: 2813-2830).

In certain embodiments, genetic modifications will utilize a sacB-based system for unmarked exchange of alleles due to the sucrose sensitivity provided by sacB expression. This may include the pCM433 vector originally tested with *M. extorquens* (Marx, C. J. et al. *BMC Research Notes* (2008) 1:1).

In certain embodiments of the present invention that utilize heterologous isoprenoid biosynthesis polypeptides, the source organisms include as non-limiting examples fungi of the genera *Blakeslea, Candida, Cryptococcus, Cunninghamella, Lipomyces, Mortierella, Mucor, Phycomyces, Pythium, Rhodosporidium, Rhodotorula, Trichosporon, Yarrowia, Aspergillus, Botrytis, Cercospora, Fusarium (Gibberella), Kluyveromyces, Neurospora, Penicillium, Pichia (Hansenula), Puccinia, Saccharomyces, Schizosaccharomyces, Sclerotium, Trichoderms, Ustilago,* and *Xanthophyllomyces (Phaffia).* In certain embodiments, the source organisms are of a species including, but not limited to, *Cryptococcus neoformans, Fusarium fujikuroi, Kluyverimyces lactis, Neurospora crassa, Saccharomyces cerevisiae, Schizosaccharomyces pombe, Ustilago maydis,* and *Yarrowia lipolytica.* In certain embodiments the source organism includes bacteria of the *Methylobacterium* genus or preferably species such as *M. extorquens.*

*Methylobacterium* strains are a diverse genus of largely plant-associated microbes. As of the past half-decade, genome sequences for several strains have been published, including *M. extorquens* AM1, *M. extorquens* DM4, *M. extorquens* CM4, *M. extorquens* PA1, *M. extorquens* BJ001 (formerly *M. populi*), *M. radiotolerans, M. nodulans,* and *Methylobacterium* spp. 4-46 (Vuileumier et al., 2009. *PLoS One*; Marx et al., 2012. *J. Bacteriology*). These strains offer various advantages and disadvantages, ranging from distinct growth rates on various substrates, to stark differences in genome size and mobile genetic element content. *M. extorquens* strains—of which there are five sequenced—pose the particular advantage of being able to draw from the tremendous knowledge about *M. extorquens* AM1, which has served as a workhorse for all of methylotrophy. Given recent discovery of a series of issues with the modern AM1 strain (Carroll et al., 2014. *BMC Microbiology*), however, some efforts have now focused on the genome streamlined, more robustly growing PA1 strain. These strains all share the majority of their genome content, and these genes are mainly 98% amino acid identical, or above. There are differences in gene content, however, which can be of critical importance to certain traits (Vuilleumier et al., 2009. *PLoS One*). As such, while a given genetic manipulation is likely to behave similarly across strains, there is also precedent for the occasional major differences.

Thus, in some embodiments, modified bacterium is a strain of *Methylobacterium*, e.g., *M. extorquens* AM1, *M. extorquens* DM4, *M. extorquens* CM4, *M. extorquens* PA1, *M. extorquens* BJ001 (formerly *M. populi*), *M. radiotolerans, M. nodulans,* and *Methylobacterium* spp. 4-46.

To date, there are three ways to generate carotenoid variants of *Methylobacterium*. First, key genes such as crtI can be knocked out that eliminate all coloration (Van Dien et al., 2003. *Applied & Environmental Microbiology*). Second, genes can be removed from branches that divert biosynthesis away from carotenoids, thereby enhancing coloration. An example of this is deleting shc, and thus the production of hopanoids. Finally, evolved variants from selection for growth in other conditions, such as rapid growth on 15 mM methanol (Lee et al., 2009. *Evolution*), can fortuitously lead to strains with increased or varied coloration.

In certain embodiments, methylotrophic bacteria of the invention are characterized in that they are genetically modified or artificially pre-selected to produce elevated levels of a carotenoid compound relative to the corresponding unmodified or unselected bacterium. Improved carotenoid production can be assayed in terms of mg carotenoid per gram of dry cell weight, such as using the methods described in Lemuth et al., 2011 (*Microbial Cell Factories.* 10:29). In some embodiments, the bacterial production of at least one carotenoid compound is elevated by at least 10%, 15%, 20%, 25%, 50%, 80%, 100%, 200%, 300%, 400%, 500%, 1000% or more.

The isoprenoid biosynthesis pathway is also used by organisms to produce non-carotenoid compounds, such as sterols, steroids, and vitamins, including vitamin E or vitamin K. Proteins that have isoprenoid biosynthesis pathway intermediates as their substrates, and divert them into biosynthesis of non-carotenoid compounds, are indirect inhibitors of carotenoid biosynthesis because they compete for the same intermediates as the desired carotenoid pathway. The present invention addresses this issue by enabling reductions of the level or activity of such competing proteins, allowing for increased production of carotenoid compounds.

Beyond carotenoids and vitamins, a number of amino acids and other small metabolites are at limiting levels in feed sources. These may be amino acids, and in particular the set of arginine, threonine, valine, lysine, and methionine. Another molecule of interest is taurine (2-aminoethanosulfonic acid). In certain embodiments, directed genetic modifications of the relevant amino acid and taurine biosynthetic pathways augments the expression of key genes or removes side pathways and recycling pathways. In other embodiments selection may involve use of toxic analogues of the relevant compounds, such as ethionine to achieve methionine overproduction (see Lawrence et al. *Genetics* (1968) 58: 473-492). In yet other embodiments, experimental evolution of overproduction may occur through selection in the context of metabolic cross-feeding (Harcombe, W. R. *Evolution* (2010), 64(7), 2166-2172). In other embodiments, manipulations obtained by directed engineering, selection with analogues, and selection in consortia will be combined.

Carotenoids produced according to the present invention can be utilized in any of the applications mentioned herein, among which are their multifaceted biological or nutritional properties (antioxidant, antiproliferative, etc.) and their usefulness as pigments ranging in color from yellow to red. For example, according to the present invention, carotenoids may be used in pharmaceuticals (see, for example, Bertram et al., *Nutr. Rev.* 1999, 57:182; Singh et al., *Oncology* 1998, 12:1643; Rock, *Pharmacol. Ther.* 1997, 75:185; Edge et al., *J. Photochem Photobiol* 1997, 41:189; U.S. Patent Application 2004/0116514 (incorporated by reference); U.S. Patent Application 2004/0259959 (incorporated by reference)), food supplements (see, for example, Koyama et al., *J. Photochem Photobiol* 1991, 9:265; Bauemfeind, *Carotenoids as colorants and vitamin A precursors*, Academic Press, NY, 1981; U.S. Patent Application 2004/0115309 (incorporated by reference); U.S. Patent Application 2004/0234579 (incorporated by reference)), electro-optic applications, animal feed additives (see for example Krinski, *Pure Appl. Chem.* 1994, 66:1003; Polazza et al., *Meth. Enzymol.* 1992, 213:403), cosmetics (as anti-oxidants and/or as cosmetics, including fragrances; see, for example, U.S. Patent Application 2004/0127554 (incorporated by reference)), etc. Carotenoids produced in accordance with the present invention may also be used as intermediates in the production of other compounds (e.g., steroids).

For example, astaxanthin and/or esters thereof may be useful in a variety of pharmaceutical applications and health foods including treatment of inflammatory diseases, asthma, atopic dermatitis, allergies, multiple myeloma, arteriosclerosis, cardiovascular disease, liver disease, cerebrovascular disease, thrombosis, neoangiogenesis-related diseases, including cancer, rheumatism, diabetic retinopathy; macular degeneration and brain disorder, hyperlipidemia, kidney ischemia, diabetes, hypertension, tumor proliferation and metastasis; and metabolic disorders. Additionally, carotenoids and astaxanthin may be useful in the prevention and treatment of fatigue, for improving kidney function in nephropathy from inflammatory diseases, as well as prevention and treatment of other life habit-related diseases. Still further, astaxanthin has been found to play a role as inhibitors of various biological processes, including interleukin inhibitors, phosphodiesterase inhibitors, phospholipase A2 inhibitors, cyclooxygenase-2 inhibitors, matrix metalloproteinase inhibitors, capillary endothelium cell proliferation inhibitors, lipoxygenase inhibitors. See, for example, Japanese Publication No. 2006022121 (JP Appl No. 2005-301156); Japanese Publication No. 2006016408 (JP Appl No. 2005-301155); Japanese Publication No. 2006016409 (JP Appl No. 2005-301157); Japanese Publication No. 2006016407 (JP Appl No. 2005-301153); Japanese Publication No. 2006008717 (JP Appl No. 2005-301151); Japanese Publication No. 2006008716 (JP Appl No. 2005-301150); Japanese Publication No. 2006008720 (JP Appl No. 2005-301158); Japanese Publication No. 2006008719 (JP Appl No. 2005-301154); Japanese Publication No. 2006008718 (JP Appl No. 2005-301152); Japanese Publication No. 2006008713 (JP Appl No. 2005-301147); Japanese Publication No. 2006008715 (JP Appl No. 2005-301149); Japanese Publication No. 2006008714 (JP Appl No. 2005-301148); and Japanese Publication No. 2006008712 (JP Appl No. 2005-301146).

It will be appreciated that, in some embodiments of the invention, carotenoids produced by manipulated host cells as described herein are incorporated into a final product (e.g., food or feed supplement, pharmaceutical, cosmetic, dye-containing item, fragrance, nutraceutical, etc.) in the context of the host cell. For example, host cells may be lyophilized, freeze dried, frozen or otherwise inactivated, and then whole cells may be incorporated into or used as the final product. The host cell may also be processed prior to incorporation in the product to increase bioavailability (e.g., via lysis). This may include methods such as homogenization, with or without subsequent addition of ethoxyquin or other appropriate reductants to protect carotenoids or other nutritional components from subsequent oxidation. The host cell may be processed in the presence of a hydrophobic substance that may or may not be incorporated into the final formulation in order to aid in partial extraction and bioavailability of carotenoids. This may involve combining bacterial material with the fish oils, or other dietary oils prior to their joint addition to the eventual feed. Cell material may be provided as thawed "wet" cell material, or as dried bacterial "cake". Alternatively or additionally, a final product may incorporate only a portion of the host cell (e.g., fractionated by size, solubility), separated from the whole. For example, in some embodiments of the invention, lipid droplets are isolated from the host cells and are incorporated into or used as the final product; or a protein isolate may be incorporated into or used as the final product. In other embodiments, the carotenoids themselves, or individual carotenoid compounds are isolated and reformulated into the final product.

As stated above, fatty acid and glucoside esters are the predominant carotenoid esters found in nature, whereas additional esters (e.g., with organic acids or inorganic phosphate) can be synthesized to generate useful product forms. For delivery, carotenoid esters can also be formulated as salts of the ester form. See, e.g., US Publication No. 2005/0096477 (incorporated by reference).

The amount of carotenoid incorporated into a given product may vary dramatically depending on the product, and the particular carotenoid(s) involved. Amounts may range, for example, from less than 0.01% by weight of the product, to more than 1%, 10%, 20%, 30% or more; in some cases the carotenoid may comprise 100% of the product. Similarly, the addition of cell material in feed can range from small doses, such as 0.01%, up to 100% of the feed. In some embodiment, the feed contains at least 1%, 5%, 10%, 15%, 20%, 25%, 30%, 50% or more of biomass of the invention.

In some embodiments of the invention, one or more produced carotenoids is incorporated into a component of food or feed (e.g., a food supplement). Types of food products into which carotenoids can be incorporated according to the present invention are not particularly limited, and include beverages, such as teas, juices, and liquors; confections, such as jellies and biscuits; fat-containing foods and beverages, such as dairy products; processed food products, such as rice and soft rice (or porridge); infant formulas; or the like. In some embodiments, it may be useful to incorporate the carotenoids within bodies of edible lipids as it may facilitate incorporation into certain fat-containing food products.

Examples of feedstuffs into which carotenoids produced in accordance with the present invention may be incorporated include, for instance, pet foods, such as cat foods, dog foods and the like, feeds for aquarium fish, cultured fish or crustaceans, etc., feed for farm-raised animals (including livestock and further including fish or crustaceans raised in aquaculture). The carotenoids and/or other caloric or nutritional supplements produced in accordance with the present invention can also be incorporated into food or vitamin supplements for human consumption. Food or feed material into which the carotenoid(s) produced in accordance with the present invention is incorporated is preferably palatable to the organism which is the intended recipient. This food or feed material may have any physical properties currently known for a food material (e.g., solid, liquid, soft).

In some embodiments of the invention, one or more produced carotenoids is incorporated into a cosmetic product. Examples of such cosmetics include, for instance, skin cosmetics (e.g., lotions, emulsions, creams and the like), lipsticks, anti-sunburn cosmetics, makeup cosmetics, fragrances, and other products for daily use (e.g., toothpastes, mouthwashes, bad breath preventive agents, solid soaps, liquid soaps, shampoos, conditioners).

In some embodiments, one or more produced carotenoids are incorporated into a pharmaceutical. Examples of such pharmaceuticals include, for instance, various types of tablets, capsules, drinkable agents, troches, gargles, etc. In some embodiments, the pharmaceutical is suitable for topical application. Dosage forms are not particularly limited, and include capsules, oils, granula, granula subtilae, pulveres, tabellae, pilulae, trochisci, or the like. Oils and oil-filled capsules may provide additional advantages both because of their lack of ingredient decomposition during manufacturing, and because inventive carotenoid-containing lipid droplets may be readily incorporated into oil-based formulations.

Pharmaceuticals according to the present invention may be prepared according to techniques established in the art including, for example, the common procedure as described in the United States Pharmacopoeia.

Carotenoids produced according to the present invention may be incorporated into any pigment-containing product including, for example, fabric, and paint. They may also be incorporated into a product which is an environmental indicator, or an instrument, such as a biosensor, for use as a detection agent.

Accordingly, the present invention further provides a process for production of carotenoids, such as, but not limited to, β-carotene, echinenone, β-cryptoxanthin, canthaxanthin, adonirubin, cis-adonixanthin, adonixanthin, astaxanthin, zeaxanthin, spirilloxanthin, and intermediates leading to spirilloxanthin, such as lycopene and rhodopin, the process comprising culturing a bacterial species in a nutrient medium including sources of carbon, nitrogen and inorganic substances; and recovering an individual carotenoid pigment or a mixture of carotenoid pigments from the bacterial cells, vesicles secreted therefrom and/or the growth medium.

Medium for production of carotenoids using the present microorganisms is, for example, as follows. It contains a carbon source, a nitrogen source and inorganic salts necessary for the growth of producer microorganisms, as well as, if necessary, any special required substances for the growth or thriving of the organism (for example, vitamins, amino acids, nucleic acids).

The carbon source may comprise sugars, such as glucose, sucrose, lactose, fructose, trehalose, mannose, mannitol, and maltose; organic acids, such as acetic acid, fumaric acid, citric acid, propionic acid, malic acid, pyruvic acid, malonic acid, and ascorbic acid; alcohols, such as ethanol, propanol, butanol, pentanol, hexanol, isobutanol, and glycerol; oil or fat, such as soybean oil, rice bran oil, olive oil, corn oil, sesame oil, linseed oil, and the like. The amount of the carbon source added varies according to the kind of the carbon source, and usually 1 to 100 g, or 2 to 50 g per liter of medium.

The nitrogen source may comprise potassium nitrate, ammonium nitrate, ammonium chloride, ammonium sulfate, ammonium phosphate, ammonia, urea, and the like, alone or in combination. Amount of the nitrogen source added varies according to the kind of the nitrogen source, and is usually 0.1 to 30 g, and preferably 1 to 10 g per liter of medium.

The inorganic salt may comprise potassium dihydrogen phosphate, dipotassium hydrogen phosphate, disodium hydrogen phosphate, magnesium sulfate, magnesium chloride, ferric sulfate, ferrous sulfate, ferric chloride, ferrous chloride, manganous sulfate, manganous chloride, zinc sulfate, zinc, chloride, cupric sulfate, calcium chloride, calcium carbonate, sodium carbonate, and the like, alone or in combination. Amount of inorganic salt varies according to the kind of the inorganic salt, and usually 0.001 to 10 g per liter of medium.

As special required substances, vitamins, nucleic acids, yeast extract, peptone, meat extract, malt extract, corn steep liquor, soybean meal, dried yeast etc., may be used alone or in combination. Amount of the special required substance used varies according to the kind of the substance, and usually ranges between 0.2 g to 200 g, and preferably 3 to 100 g per liter of medium.

The pH value of a medium is typically adjusted to pH 2 to 12, preferably 6 to 9. The medium may further comprise one or more buffers to maintain the culture at the desired pH. Typical buffers are known in the art and include phosphate, carbonate, acetate, PIPES, HEPES, and Tris buffers; the optimal buffer for a given organism can easily be determined by one of ordinary skill in the art. For *Methylobacterium*, a common medium (Lee, M.-C. et al. *Evolution* (2009) 63: 2813-2830) is a phosphate buffered medium that consists of 1 mL of trace metal solution (to 1 liter of deionized water the following were added in this order: 12.738 g of EDTA disodium salt dihydrate, 4.4 g of $ZnSO_4.7H_2O$, 1.466 g of $CaCl_2.2H_2O$, 1.012 g of $MnCl_2.4H_2O$, 0.22 g of $(NH_4)_6Mo_7O_{24}.4H_2O$, 0.314 g of $CuSO_4.5H_2O$, 0.322 g of $CoCl_2.6H_2O$, and 0.998 g of $FeSO_4.7H_2O$; pH 5.0 was maintained after every addition), 100 mL of phosphate buffer (25.3 g of $K_2HPO_4$ and 22.5 g of $NaH_2PO_4$ in 1 liter of deionized water), 100 mL of sulfate solution (5 g of $(NH_4)_2SO_4$ and 0.98 g of $MgSO_4$ in 1 liter of deionized water), and 799 mL of deionized water. All components were heat sterilized separately and then pooled together. An alternative medium recently developed for use with *Methylobacterium extorquens* takes advantage of an organic buffer and has a citrate-chelated trace metal mix. Culturing is carried out at temperature of 15 to 40° C., and preferably 20 to 35° C., usually for 1 to 20 days, and preferably 1 to 4 days, under aerobic condition provided by shaking or aeration/agitation. Common practice with *Methylobacterium* is at 30° C. As a membrane component, carotenoids may be produced to higher titer at temperatures that vary from optimal, in medium that becomes limiting for a nutrient such as N or P, by exposure to light (visible or ultraviolet), or by the addition of a stressful agent such as NaCl. Finally the carotenoid(s) and other product nutrients may be isolated and purified from the culture.

Figure 2:
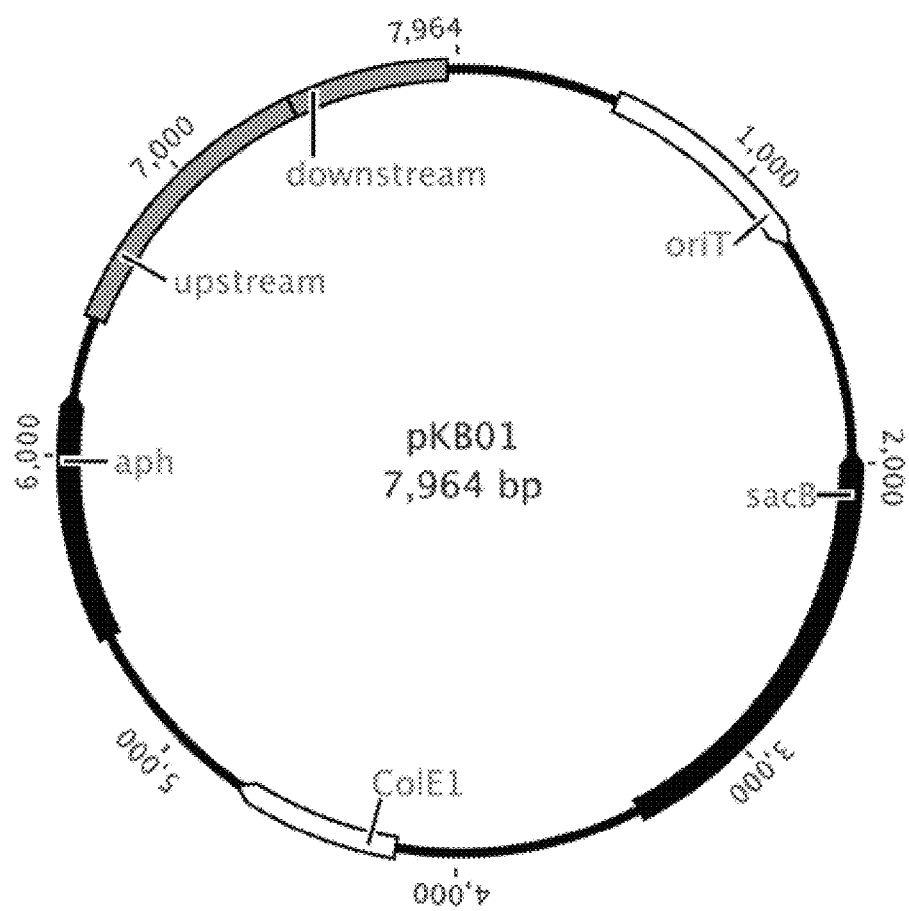
FIG. 2 shows a map of pKB01: deletion construct for crtI-like gene, Mext_3011, described in Example 7.

The protocol for making M-PIPES medium is described in Table S1 of Delaney et al., 2013. PLoS One (8:e62957). FIG. 2 in U.S. Ser. No. 61/863,701 shows an exemplary recipe for medium optimized for use with *M. extorquens*.

In order to generate dense cultures of strains such as *Methylobacterium*, it may be advantageous to use a fed-batch method. Methanol can be tolerated well at 0.5-1% v/v (~120-240 mM), and thus this step size of addition can be used repeatedly. Critically, pH levels drop during culturing on methanol, such that the use of a base such as KOH or NaOH would be important to maintain the pH around 6.5. Aeration can be achieved via physical agitation, such as an impeller, via bubbling of filtered air or pure oxygen, or in combination. In order to reduce production costs, the buffer can be replaced from phosphates or PIPES to a carbonate-buffered medium.

Typically, microbial cells are separated from the culture by a conventional means such as centrifugation or filtration. The cells may be isolated whole, or may be lysed to release their contents for extraction or further processing. The cells or the medium may be subjected to an extraction with a suitable solvent. As an optional step prior to extraction carotenoid loaded vesicles may be recovered from the medium, by for example, ultracentrifugation or filtration.

As a solvent for the extraction, any substance in which the carotenoids are soluble can be used. For example, organic solvents, such as acetone, chloroform, dichloromethane, hexane, cyclohexane, methanol, ethanol, isopropanol, benzene, carbon disulfide, and diethyl ether, are used, and preferably chloroform, dichloromethane, acetone, methanol, ethanol or isopropanol is used. The purification can be carried out by conventional procedures, such as absorption, elution, dissolving and the like, alone or preferably in combination.

According to the present invention, one or more of β-carotene, echinenone, β-cryptoxanthin, canthaxanthin, adonirubin, cis-adonixanthin, adonixanthin, astaxanthin, zeaxanthin, spirilloxanthin, and intermediates leading to spirilloxanthin such as lycopene and rhodopin are simultaneously produced and present in the cultured cells and/or medium.

One aspect of the invention is related to a method for the production of a carotenoid compound, the method comprising
(a) providing a pigmented methylotrophic bacterial host cell comprising:
(i) suitable levels of isopentenyl pyrophosphate for the production of the carotenoid compound; and (ii) at least one isolated nucleic acid molecule encoding an enzyme in the carotenoid biosynthetic pathway under the control of suitable regulatory sequences;
(b) contacting the host cell of step (a) under suitable growth conditions with an effective amount of a C1 carbon substrate whereby the carotenoid compound is produced.

In certain embodiments, the carotenoid compound is selected from the group consisting of non-natural carotenoids, antheraxanthin, adonixanthin, astaxanthin, canthaxanthin, capsorubrin, β-cryptoxanthin, α-carotene, β-carotene, ε-carotene, echinenone, γ-carotene, f-carotene, α-cryptoxanthin, diatoxanthin, 7,8-didehydroastaxanthin, fucoxanthin, fucoxanthinol, isorenieratene, lactucaxanthin, lutein, lycopene, neoxanthin, neurosporene, hydroxyneurosporene, peridinin, phytoene, rhodopin, rhodopin glucoside, siphonaxanthin, spheroidene, spheroidenone, spirilloxanthin, uriolide, uriolide acetate, violaxanthin, zeaxanthin-β-diglucoside, zeaxanthin, and intermediates in the biosynthetic production of any of the foregoing carotenoid compounds.

In certain embodiments, the carotenoid compound is selected from the group consisting of β-carotene, lycopene, rhodopin, echinenone, β-cryptoxanthin, canthaxanthin, adonirubin, cis-adonixanthin, adonixanthin, astaxanthin, zeaxanthin, spirilloxanthin, and intermediates in the biosynthetic production of any of the foregoing carotenoid compounds.

In certain embodiments, the carotenoid compound is selected from the group consisting of β-carotene, lycopene, rhodopin, astaxanthin and spirilloxanthin.

In certain embodiments, the carotenoid compound is spirilloxanthin.

In certain embodiments, the C1 carbon substrate is selected from the group consisting of methane, methanol, formaldehyde, formic acid, methylated amines, methylated thiols, and carbon dioxide.

In certain embodiments, the C1 carbon substrate is selected from the group consisting of methanol, formaldehyde, and methylated amines.

In certain embodiments, the C1 carbon substrate is methanol.

In certain embodiments, the host cell is selected from the group consisting of *Methylomonas, Methylobacter, Methylococcus, Methylosinus, Methylocyctis, Methylomicrobium, Methanomonas, Methylophilus, Methylobacillus, Methylobacterium, Hyphomicrobium, Xanthobacter, Bacillus, Paracoccus, Nocardia, Arthrobacter, Rhodopseudomonas, Pseudomonas, Candida, Hansenula, Pichia, Torulopsis,* and *Rhodotorula.*

In certain embodiments, the host cell is a *Methylobacterium.*

In certain embodiments, the host cell is *Methylobacterium extorquens.*

In certain embodiments, the host cell comprises a functional Embden-Meyerhof carbon pathway, said pathway comprising a gene encoding a pyrophosphate dependent phosphofructokinase enzyme.

In certain embodiments, the host cell contains at least one gene encoding a fructose bisphosphate aldolase enzyme.

In certain embodiments, the host cell contains a functional Entner-Douderoff carbon pathway.

In certain embodiments, the suitable levels of isopentenyl pyrophosphate are provided by the expression of heterologous upper isoprenoid pathway genes.

In certain embodiments, the upper isoprenoid pathway genes are selected from the group consisting of D-1-deoxyxylulose-5-phosphate synthase (Dxs), D-1-deoxyxylulose-5-phosphate reductoisomerase (Dxr), 2C-methyl-D-erythritol cytidylyltransferase (IspD), 4-diphosphocytidyl-2-C-methylerythritol kinase (IspE), 2C-methyl-D-erythritol 2,4-cyclodiphosphate synthase (IspF), CTP synthase (PyrG), LytB, and GcpE.

In certain embodiments, the host cell produces a non-natural spectrum of carotenoid compounds.

In certain embodiments, the host cell produces a spectrum of amino acids suitable for use as a nutritional supplement.

In certain embodiments, the spectrum of amino acids comprises all essential amino acids.

In certain embodiments, the host cell produces taurine.

In certain embodiments, the host cell produces one or more vitamins or antioxidants.

In certain embodiments, the host cell produces one or more fatty acids.

In certain embodiments, the one or more fatty acids comprises monounsaturated fatty acids, polyunsaturated fatty acids, or one or more essential omega-3 fatty acids.

In certain embodiments, the one or more essential omega-3 fatty acids is EPA, DHA, or both.

In certain embodiments, the host cell is a spontaneous mutant which overexpresses one or more carotenoid compounds relative to the non-mutant cell.

In certain embodiments, the isolated nucleic acid molecule encodes a carotenoid biosynthetic enzyme selected from the group consisting of geranylgeranyl pyrophosphate (GGPP) synthase, phytoene synthase, phytoene desaturase, lycopene cyclase, β-carotene hydroxylase, zeaxanthin glucosyl transferase, β-carotene ketolase, β-carotene C-4 oxygenase, β-carotene desaturase, spheroidene monooxygenase, carotene hydratase, carotenoid 3,4-desaturase, 1-OH-carotenoid methylase, farnesyl diphosphate synthetase, and diapophytoene dehydrogenase.

In certain embodiments, the host cell is a transformed cell comprising multiple copies of at least one gene encoding an enzyme selected from the group consisting of D-1-deoxyxylulose-5-phosphate synthase (Dxs), D-1-deoxyxylulose-5-phosphate reductoisomerase (Dxr), 2C-methyl-D-erythritol cytidylyltransferase (IspD), 4-diphosphocytidyl-2-C-methylerythritol kinase (IspE), 2C-methyl-D-erythritol 2,4-cyclodiphosphate synthase (IspF), CTP synthase (PyrG), LytB, GcpE, isopentyl diphosphate isomerase, farnesyl diphosphate synthase, geranylgeranyl diphosphate synthase, phytoene synthase, phytoene desaturase, lycopene cyclase (CrtY), β-carotene ketolase (CrtW), and β-carotene hydroxylase (CrtZ).

In certain embodiments, the host cell is a transformed cell comprising at least one gene encoding an enzyme selected from the group consisting of D-1-deoxyxylulose-5-phosphate synthase (Dxs), D-1-deoxyxylulose-5-phosphate reductoisomerase (Dxr), 2C-methyl-D-erythritol cytidylyltransferase (IspD), 4-diphosphocytidyl-2-C-methylerythritol kinase (IspE), 2C-methyl-D-erythritol 2,4-cyclodiphosphate synthase (IspF), CTP synthase (PyrG), LytB, GcpE, isopentyl diphosphate isomerase, farnesyl diphosphate synthase, geranylgeranyl diphosphate synthase, phytoene synthase, phytoene desaturase, lycopene cyclase (CrtY), β-carotene ketolase (CrtW), and β-carotene hydroxylase (CrtZ), operably linked to a strong promoter.

In certain embodiments, the host cell comprises at least one gene encoding an enzyme selected from the group consisting of lycopene cyclase (CrtY), β-carotene ketolase (CrtW), and β-carotene hydroxylase (CrtZ).

In certain embodiments, the host cell comprises one or more of the genes CrtY (lycopene cyclase) from *Bradyrhizobium* sp. ORS 278 [GenBank sequence ID: YP_001208335.1], CrtW (beta-carotene ketolase) from *Bradyrhizobium* sp. ORS 278 [GenBank sequence ID: YP_001208332.1], and CrtZ (β-carotene hydroxylase) from *Brevundimonas* sp. SD212 [GenBank sequence ID: AB181388].

In certain embodiments, the host cell is modified so that one or more genes producing enzymes that divert isoprenoid compounds from the carotenoid biosynthetic pathway are blocked or deleted.

In certain embodiments, the one or more blocked or deleted genes are selected from the group consisting of genes involved in hopanoid biosynthesis, genes involved in producing carotenoids other than astaxanthin, and genes involved in producing carotenoids other than spirilloxanthin.

In certain embodiments, the one or more blocked or deleted genes are selected from the group consisting of hpnC, hpnD, hpnE, she (hpnF), bchG, bchP, crtC, crtD, and crtF.

In certain embodiments, the host cell is a spontaneous mutant whose rate of growth is increased relative to a corresponding non-mutant.

In certain embodiments, the host cell is cultured under stress conditions selected from light depletion, nutrient depletion, nitrogen depletion, high salt, or a chemical that inhibits growth of the host cell, wherein the stress conditions induce changes in gene expression leading to increased carotenoid production.

One aspect of the present invention is a pigmented methylotrophic host cell that produces a carotenoid compound, comprising:
(i) suitable levels of isopentenyl pyrophosphate for the production of the carotenoid compound; and (ii) at least one isolated nucleic acid molecule encoding an enzyme in the carotenoid biosynthetic pathway under the control of suitable regulatory sequences; wherein the host cell produces a carotenoid compound.

In certain embodiments, the carotenoid compound is selected from the group consisting of non-natural carotenoids, antheraxanthin, adonixanthin, astaxanthin, canthaxanthin, capsorubrin, β-cryptoxanthin, α-carotene, β-carotene, ε-carotene, echinenone, γ-carotene, ƒ-carotene, α-cryptoxanthin, diatoxanthin, 7,8-didehydroastaxanthin, fucoxanthin, fucoxanthinol, isorenieratene, lactucaxanthin, lutein, lycopene, neoxanthin, neurosporene, hydroxyneurosporene, peridinin, phytoene, rhodopin, rhodopin glucoside, siphonaxanthin, spheroidene, spheroidenone, spirilloxanthin, uriolide, uriolide acetate, violaxanthin, zeaxanthin-β-diglucoside, zeaxanthin, and intermediates in the biosynthetic production of any of the foregoing carotenoid compounds.

In certain embodiments, the carotenoid compound is selected from the group consisting of β-carotene, lycopene, rhodopin, echinenone, β-cryptoxanthin, canthaxanthin, adonirubin, cis-adonixanthin, adonixanthin, astaxanthin, zeaxanthin, spirilloxanthin, and intermediates in the biosynthetic production of any of the foregoing carotenoid compounds.

In certain embodiments, the carotenoid compound is selected from the group consisting of β-carotene, lycopene, rhodopin, astaxanthin and spirilloxanthin.

In certain embodiments, the carotenoid compound is spirilloxanthin.

In certain embodiments, the host cell is capable of using as an energy source a C1 carbon substrate selected from the group consisting of methane, methanol, formaldehyde, formic acid, methylated amines, methylated thiols, and carbon dioxide.

In certain embodiments, the C1 carbon substrate is selected from the group consisting of methanol, formaldehyde, and methylated amines.

In certain embodiments, the C1 carbon substrate is methanol.

In certain embodiments, the host cell is selected from the group consisting of *Methylomonas, Methylobacter, Methylococcus, Methylosinus, Methylocyctis, Methylomicrobium, Methanomonas, Methylophilus, Methylobacillus, Methylobacterium, Hyphomicrobium, Xanthobacter, Bacillus, Paracoccus, Nocardia, Arthrobacter, Rhodopseudomonas, Pseudomonas, Candida, Hansenula, Pichia, Torulopsis*, and *Rhodotorula*.

In certain embodiments, the host cell is a *Methylobacterium*.

In certain embodiments, the host cell is *Methylobacterium extorquens*.

In certain embodiments, the host cell comprises a functional Embden-Meyerhof carbon pathway, said pathway comprising a gene encoding a pyrophosphate dependent phosphofructokinase enzyme.

In certain embodiments, the host cell contains at least one gene encoding a fructose bisphosphate aldolase enzyme.

In certain embodiments, the host cell contains a functional Entner-Douderoff carbon pathway.

In certain embodiments, the suitable levels of isopentenyl pyrophosphate are provided by the expression of heterologous upper isoprenoid pathway genes.

In certain embodiments, the upper isoprenoid pathway genes are selected from the group consisting of D-1-deoxyxylulose-5-phosphate synthase (Dxs), D-1-deoxyxylulose-5-phosphate reductoisomerase (Dxr), 2C-methyl-D- erythritol cytidylyltransferase (IspD), 4-diphosphocytidyl-2-C-methylerythritol kinase (IspE), 2C-methyl-D-erythritol 2,4-cyclodiphosphate synthase (IspF), CTP synthase (PyrG), LytB, and GcpE.

In certain embodiments, the host cell produces a non-natural spectrum of carotenoid compounds.

In certain embodiments, the host cell produces a spectrum of amino acids suitable for use as a nutritional supplement.

In certain embodiments, the spectrum of amino acids comprises all essential amino acids.

In certain embodiments, the host cell produces taurine.

In certain embodiments, the host cell produces one or more vitamins or antioxidants.

In certain embodiments, the host cell produces one or more fatty acids.

In certain embodiments, the one or more fatty acids comprises monounsaturated fatty acids, polyunsaturated fatty acids, or one or more essential omega-3 fatty acids.

In certain embodiments, the one or more essential omega-3 fatty acids is EPA, DHA, or both.

In certain embodiments, the host cell is a spontaneous mutant which overexpresses one or more carotenoid compounds relative to the non-mutant cell.

In certain embodiments, the isolated nucleic acid molecule encodes a carotenoid biosynthetic enzyme selected from the group consisting of geranylgeranyl pyrophosphate (GGPP) synthase, phytoene synthase, phytoene desaturase, lycopene cyclase, β-carotene hydroxylase, zeaxanthin glucosyl transferase, β-carotene ketolase, β-carotene C-4 oxygenase, β-carotene desaturase, spheroidene monooxygenase, carotene hydratase, carotenoid 3,4-desaturase, 1-OH-carotenoid methylase, farnesyl diphosphate synthetase, and diapophytoene dehydrogenase.

In certain embodiments, the host cell is a transformed cell comprising multiple copies of at least one gene encoding an enzyme selected from the group consisting of D-1-deoxyxylulose-5-phosphate synthase (Dxs), D-1-deoxyxylulose-5-phosphate reductoisomerase (Dxr), 2C-methyl-D-erythritol cytidylyltransferase (IspD), 4-diphosphocytidyl-2-C-methylerythritol kinase (IspE), 2C-methyl-D-erythritol 2,4-cyclodiphosphate synthase (IspF), CTP synthase (PyrG), LytB, GcpE, isopentyl diphosphate isomerase, farnesyl diphosphate synthase, geranylgeranyl diphosphate synthase, phytoene synthase, phytoene desaturase, lycopene cyclase (CrtY), β-carotene ketolase (CrtW), and β-carotene hydroxylase (CrtZ).

In certain embodiments, the host cell is a transformed cell comprising at least one gene encoding an enzyme selected from the group consisting of D-1-deoxyxylulose-5-phosphate synthase (Dxs), D-1-deoxyxylulose-5-phosphate reductoisomerase (Dxr), 2C-methyl-D-erythritol cytidylyltransferase (IspD), 4-diphosphocytidyl-2-C-methylerythritol kinase (IspE), 2C-methyl-D-erythritol 2,4-cyclodiphosphate synthase (IspF), CTP synthase (PyrG), LytB, GcpE, isopentyl diphosphate isomerase, farnesyl diphosphate synthase, geranylgeranyl diphosphate synthase, phytoene synthase, phytoene desaturase, lycopene cyclase (CrtY), β-carotene ketolase (CrtW), and β-carotene hydroxylase (CrtZ), operably linked to a strong promoter.

In certain embodiments, the host cell comprises at least one gene encoding an enzyme selected from the group consisting of lycopene cyclase (CrtY), β-carotene ketolase (CrtW), and β-carotene hydroxylase (CrtZ).

In certain embodiments, the host cell comprises one or more of the genes CrtY (lycopene cyclase) from *Bradyrhizobium* sp. ORS 278 [GenBank sequence ID: YP_001208335.1], CrtW (beta-carotene ketolase) from *Bradyrhizobium* sp. ORS 278 [GenBank sequence ID: YP_001208332.1], and CrtZ (β-carotene hydroxylase) from *Brevundimonas* sp. SD212 [GenBank sequence ID: AB181388].

In certain embodiments, the host cell is modified so that one or more genes producing enzymes that divert isoprenoid compounds from the carotenoid biosynthetic pathway are blocked or deleted.

In certain embodiments, the one or more blocked or deleted genes are selected from the group consisting of genes involved in hopanoid biosynthesis, genes involved in producing carotenoids other than astaxanthin, and genes involved in producing carotenoids other than spirilloxanthin.

In certain embodiments, the one or more blocked or deleted genes are selected from the group consisting of hpnC, hpnD, hpnE, she (hpnF), bchG, bchP, crtC, crtD, and crtF.

In certain embodiments, the host cell is a spontaneous mutant whose rate of growth is increased relative to a corresponding non-mutant.

In certain embodiments, the host cell is cultured under stress conditions selected from light depletion, nutrient depletion, nitrogen depletion, high salt, or a chemical that inhibits growth of the host cell, wherein the stress conditions induce changes in gene expression leading to increased carotenoid production.

In one aspect, the invention relates to a feed composition, comprising biomass from a host cell as described above.

In certain embodiments, the composition further comprises a source of protein comprising all of the essential amino acids.

In certain embodiments, the composition further comprises one or more vitamins or antioxidants.

In certain embodiments, the composition further comprises one or more fatty acids.

In certain embodiments, the one or more fatty acids comprises monounsaturated fatty acids, polyunsaturated fatty acids, or one or more essential omega-3 fatty acids.

In certain embodiments, the one or more essential omega-3 fatty acids is EPA, DHA, or both.

In certain embodiments, the biomass comprises whole cells.

In certain embodiments, the biomass comprises lysed cells.

In certain embodiments, the biomass is processed or partially processed.

In certain embodiments, the composition is for aquaculture, including aquaculture feed organisms such as krill, rotifers, or the like.

In certain embodiments, the composition is for use in agriculture as an animal feed.

In certain embodiments, the composition is for use with ornamental fish, shrimp, corals, or other hobbyist aquaculture.

In certain embodiments, the composition is for human use.

In certain embodiments, the human use is as a nutritional supplement.

In one aspect, the invention relates to a method of preparing a feed composition as described above, the method comprising
 (a) culturing in an appropriate medium at least one host cell as described above;
 (b) concentrating the medium to provide a biomass,
 (c) optionally providing additional feed components, and
 (d) producing the feed composition from the biomass.

In certain embodiments, step (b) comprises centrifugation.

In certain embodiments, step (b) comprises allowing the biomass to settle.

In certain embodiments, step (b) comprises filtration.

In certain embodiments, the method further comprises a pre-treatment of the biomass after step (a) with a chemical agent to disrupt the cell membranes of the biomass.

In certain embodiments, the chemical agent is a surfactant or solvent.

In certain embodiments, the method further comprises mechanical disruption of the cell membranes of the biomass after step (a).

In this disclosure, a number of terms and abbreviations are used. The following definitions are provided.

Carotenogenic modification: The term "carotenogenic modification", as used herein, refers to a modification of a host organism that adjusts production of one or more carotenoids, as described herein. For example, a carotenogenic modification may increase the production level of one or more carotenoids, and/or may alter relative production levels of different carotenoids. In principle, an inventive carotenogenic modification may be any chemical, physiological, genetic, or other modification that appropriately alters production of one or more carotenoids in a host organism produced by that organism as compared with the level produced in an otherwise identical organism not subject to the same modification. In most embodiments, however, the carotenogenic modification will comprise a genetic modification, typically resulting in increased production of one or more selected carotenoids. In some embodiments, the selected carotenoid is one or more of astaxanthin, β-carotene, canthaxanthin, lutein, lycopene, phytoene, zeaxanthin, modified zeaxanthin or astaxanthin (e.g., glycoside, esterified zeaxanthin or astaxanthin), spirilloxanthin, and intermediates leading to spirilloxanthin such as lycopene and rhodopin. In certain embodiments, the carotenoid is one or more xanthophylls, and/or a modification thereof (e.g., glycoside, esterified xanthophylls). In certain embodiments, the xanthophyll is selected from the group consisting of astaxanthin, lutein, zeaxanthin, lycopene, spirilloxanthin, and intermediates leading to spirilloxanthin such as rhodopin, and modifications thereof. In certain embodiments, the carotenoid is one or more of astaxanthin, β-carotene, canthaxanthin, lutein, lycopene, and zeaxanthin and/or modifications of zeaxanthin or astaxanthin. In certain embodiments, the carotenoid is β-carotene. In certain embodiments, the selected carotenoid is astaxanthin. In some embodiments, the selected carotenoid is spirilloxanthin. In certain embodiments, the selected carotenoid is astaxanthin. In some embodiments, the selected carotenoid is one or more intermediates that are precursors of spirilloxanthin such as, for example, lycopene or rhodopin.

Carotenoid: The term "carotenoid" is understood in the art to refer to a structurally diverse class of pigments derived from isoprenoid pathway intermediates. The commitment step in carotenoid biosynthesis is the formation of phytoene from geranylgeranyl pyrophosphate. Carotenoids can be acyclic or cyclic, and may or may not contain oxygen, so that the term carotenoids include both carotenes and xanthophylls. In general, carotenoids are hydrocarbon compounds having a conjugated polyene carbon skeleton formally derived from the five-carbon compound IPP, including triterpenes ($C_{30}$ diapocarotenoids) and tetraterpenes ($C_{40}$ carotenoids) as well as their oxygenated derivatives and other compounds that are, for example, $C_{35}$, $C_{50}$, $O_{60}$, $C_{70}$, $C_{80}$ in length or other lengths. Many carotenoids have strong light absorbing properties and may range in length in excess of $C_{200}$. $C_{30}$ diapocarotenoids typically consist of six isoprenoid units joined in such a manner that the arrangement of isoprenoid units is reversed at the center of the molecule so that the two central methyl groups are in a 1,6-positional relationship and the remaining non-terminal methyl groups are in a 1,5-positional relationship. Such $C_{30}$ carotenoids may be formally derived from the acyclic $C_{30}H_{42}$ structure, having a long central chain of conjugated double bonds, by: (i) hydrogenation (ii) dehydrogenation, (iii) cyclization, (iv) oxidation, (v) esterification/glycosylation, or any combination of these processes. $C_{40}$ carotenoids typically consist of eight isoprenoid units joined in such a manner that the arrangement of isoprenoid units is reversed at the center of the molecule so that the two central methyl groups are in a 1,6-positional relationship and the remaining non-terminal methyl groups are in a 1,5-positional relationship. Such $C_{40}$ carotenoids may be formally derived from the acyclic $C_{40}H_{56}$ structure, having a long central chain of conjugated double bonds, by (i) hydrogenation, (ii) dehydrogenation, (iii) cyclization, (iv) oxidation, (v) esterification/glycosylation, or any combination of these processes. The class of $C_{40}$ carotenoids also includes certain compounds that arise from rearrangements of the carbon skeleton, or by the (formal) removal of part of this structure. More than 600 different carotenoids have been identified in nature. Carotenoids include but are not limited to: antheraxanthin, adonirubin, adonixanthin, astaxanthin, canthaxanthin, capsorubrin, β-cryptoxanthin, α-carotene, β-carotene, β,ψ-carotene, δ-carotene, ε-carotene, echinenone, 3-hydroxyechinenone, 3'-hydroxyechinenone, γ-carotene, ψ-carotene, 4-keto-γ-carotene, ƒ-carotene, α-cryptoxanthin, deoxyflexixanthin, diatoxanthin, 7,8-didehydroastaxanthin, didehydrolycopene, fucoxanthin, fucoxanthinol, isorenieratene, β-isorenieratene, lactucaxanthin, lutein, lycopene, myxobactone, neoxanthin, neurosporene, hydroxyneurosporene, peridinin, phytoene, rhodopin, rhodopin glucoside, 4-keto-rubixanthin, siphonaxanthin, spheroidene, spheroidenone, spirilloxanthin, torulene, 4-keto-torulene, 3-hydroxy-4-keto-torulene, uriolide, uriolide acetate, violaxanthin, zeaxanthin-β-diglucoside, zeaxanthin, and C30 carotenoids. Additionally, carotenoid compounds include derivatives of these molecules, which may include hydroxy-, methoxy-, oxo-, epoxy-, carboxy-, or aldehydic functional groups. Further, included carotenoid compounds include ester (e.g., glycoside ester, fatty acid ester) and sulfate derivatives (e.g., esterified xanthophylls).

Isoprenoid pathway: The "isoprenoid pathway" is understood in the art to refer to a metabolic pathway that either produces or utilizes the five-carbon metabolite isopentyl pyrophosphate (IPP). As discussed herein, two different pathways can produce the common isoprenoid precursor IPP—the "mevalonate pathway" and the "non-mevalonate pathway". The term "isoprenoid pathway" is sufficiently general to encompass both of these types of pathway. Biosynthesis of isoprenoids from IPP occurs by polymerization of several five-carbon isoprene subunits. Isoprenoid metabolites derived from IPP vary greatly in chemical structure, including both cyclic and acyclic molecules. Isoprenoid metabolites include, but are not limited to, monoterpenes, sesquiterpenes, diterpenes, sterols, and polyprenols such as carotenoids.

Oleaginic modification: The term "oleaginic modification", as used herein, refers to a modification of a host organism that adjusts the desirable oleaginy of that host organism, as described herein. In some cases, the host organism will already be oleaginous in that it will have the ability to accumulate lipid to at least about 20% of its dry cell weight. It may nonetheless be desirable to apply an oleaginic modification to such an organism, in accordance with the present invention, for example to increase (or, in some cases, possibly to decrease) its total lipid accumulation, or to adjust the types or amounts of one or more particular lipids it accumulates (e.g., to increase relative accumulation of triacylglycerol). In other cases, the host organism may be non-oleaginous (though may contain some enzymatic and regulatory components used in other organisms to accumulate lipid), and may require oleaginic modification in order to become oleaginous in accordance with the present invention. The present invention also contemplates application of oleaginic modification to non-oleaginous host strains such that their oleaginicity is increased even though, even after being modified, they may not be oleaginous as defined herein. In principle, the oleaginic modification may be any chemical, physiological, genetic, or other modification that appropriately alters oleaginy of a host organism as compared with an otherwise identical organism not subjected to the oleaginic modification. In most embodiments, however, the oleaginic modification will comprise a genetic modification, typically resulting in increased production and/or activity of one or more oleaginic polypeptides. In certain embodiments, the oleaginic modification comprises at least one chemical, physiological, genetic, or other modification; in other embodiments, the oleaginic modification comprises more than one chemical, physiological, genetic, or other modification. In certain aspects where more than one modification is utilized, such modifications can comprise any combination of chemical, physiological, genetic, or other modification (e.g., one or more genetic modification and chemical or physiological modification).

The term "feed premix" refers to the crude mixture of aquaculture feed components prior to processing, optionally at high temperature, into an aquaculture feed composition that is in the form of pellets or flakes.

An aquaculture feed composition is used in the production of an "aquaculture product", wherein the product is a harvestable aquacultured species (e.g., finfish, crustaceans), which is often sold for human consumption. For example, salmon are intensively produced in aquaculture and thus are aquaculture products.

Aquaculture compositions may also be used as feed for aquaculture feed organisms such as small fish like krill, rotifers, and the like, that are food sources for larger aquaculture organisms such as carnivorous fish. In addition, aquaculture compositions described herein can be used as feed for ornamental fish, shrimp, hobbyist aquaculture, and the like, that are not intended as food for other organisms.

The term "aquaculture meat product" refers to food products intended for human consumption comprising at least a portion of meat from an aquaculture product as defined above. An aquaculture meat product may be, for example, a whole fish or a filet cut from a fish, each of which may be consumed as food. In some embodiments, such a product can be referred to as a fish or seafood product.

"Eicosapentaenoic acid" ("EPA") is the common name for cis-5,8,11,14,17-eicosapentaenoic acid. This fatty acid is a 20:5 omega-3 fatty acid. The term EPA as used in the present disclosure will refer to the acid or derivatives of the acid (e.g., glycerides, esters, phospholipids, amides, lactones, salts or the like) unless specifically mentioned otherwise.

"Docosahexaenoic acid" ("DHA") is the common name for cis-4,7,10,13,16,19-docosahexaenoic acid. It is a 22:6 omega-3 fatty acid. The term DHA as used in the present disclosure will refer to the acid or derivatives of the acid (e.g., glycerides, esters, phospholipids, amides, lactones, salts or the like) unless specifically mentioned otherwise.

As used herein the term "biomass" refers to microbial cellular material. Biomass may be produced naturally, or may be produced from the fermentation of a native host or a recombinant production host. The biomass may be in the form of whole cells, whole cell lysates, homogenized cells, partially hydrolyzed cellular material, and/or partially purified cellular material (e.g., microbially produced oil).

The term "processed biomass" refers to biomass that has been subjected to additional processing such as drying, pasteurization, disruption, etc., each of which is discussed in greater detail below.

The term "C-1 carbon substrate" refers to any carbon-containing molecule that lacks a carbon-carbon bond. Examples are methane, methanol, formaldehyde, formic acid, formate, methylated amines (e.g., mono-, di-, and tri-methyl amine), methylated thiols, and carbon dioxide. The term "C1 metabolizer" refers to a microorganism that has the ability to use a single carbon substrate as a sole source of energy and biomass. C1 metabolizers will typically be methylotrophs and/or methanotrophs capable of growth.

The term "methylotroph" means an organism capable of oxidizing organic compounds which do not contain carbon-carbon bonds. Where the methylotroph is able to oxidize $CH_4$, the methylotroph is also a methanotroph.

The term "methanotroph" means a prokaryote capable of utilizing methane as a substrate. Complete oxidation of methane to carbon dioxide occurs by aerobic degradation pathways. Typical examples of methanotrophs useful in the present invention include but are not limited to the genera *Methylomonas*, *Methylobacter*, *Methylococcus*, and *Methylosinus*.

The term "high growth methanotrophic bacterial strain" refers to a bacterium capable of growth using methane as its sole carbon and energy source.

The term "isoprenoid compound" refers to any compound which is derived via the pathway beginning with isopentenyl pyrophosphate (IPP) and formed by the head-to-tail condensation of isoprene units which may be of 5, 10, 15, 20, 30 or 40 carbons in length. There term "isoprenoid pigment" refers to a class of isoprenoid compounds which typically have strong light absorbing properties.

The term "upper isoprene pathway" refers to any of the genes and gene products (including homologs and mutants thereof, whether naturally-occurring or genetically engineered) associated with the isoprenoid biosynthetic pathway including the dxs gene (encoding 1-deoxyxylulose-5-phosphate synthase), the dxr gene (encoding 1-deoxyxylulose-5-phosphate reductoisomerase), the "ispD" gene (encoding the 2C-methyl-D-erythritol cytidyltransferase enzyme; also known as ygbP), the "ispE" gene (encoding the 4-diphosphocytidyl-2-C-methylerythritol kinase; also known as ychB), the "ispF" gene (encoding a 2C-methyl-d-erythritol 2,4-cyclodiphosphate synthase; also known as ygbB), the "pyrG" gene (encoding a CTP synthase); the "lytB" gene involved in the formation of dimethylallyl diphosphate; and the gcpE gene involved in the synthesis of 2-C-methyl-D-erythritol 4-phosphate in the isoprenoid pathway. The term "Dxs" refers to the 1-deoxyxylulose-5-phosphate synthase enzyme encoded by the dxs gene.

The term "Dxr" refers to the 1-deoxyxylulose-5-phosphate reductoisomerase enzyme encoded by the dxr gene.

The term "YgbP" or "IspD" refers to the 2C-methyl-D-erythritol cytidyltransferase enzyme encoded by the ygbP or ispD gene. The names of the gene, ygbP or ispD, are used interchangeably in this application. The names of gene product, YgbP or IspD are used interchangeably in this application.

The term "YchB" or "IspE" refers to the 4-diphosphocytidyl-2-C-methylerythritol kinase enzyme encoded by the ychB or ispE gene. The names of the gene, ychB or ispE, are used interchangeably in this application. The names of gene product, YchB or IspE are used interchangeably in this application.

The term "YgbB" or "IspF" refers to the 2C-methyl-D-erythritol 2,4-cyclodiphosphate synthase enzyme encoded by the ygbB or ispF gene. The names of the gene, ygbB or ispF, are used interchangeably in this application. The names of the gene product, YgbB or IspF, are used interchangeably in this application.

The term "PyrG" refers to a CTP synthase enzyme encoded by the pyrG gene.

The term "IspA" refers to Geranyltransferase or farnesyl diphosphate synthase enzyme as one of prenyl transferase family encoded by ispA gene. The term "LytB" refers to protein having a role in the formation of dimethylallylpyrophosphate in the isoprenoid pathway and which is encoded by lytB gene.

The term "GcpE" refers to a protein having a role in the formation of 2-C-methyl-D-erythritol 4-phosphate in the isoprenoid pathway (Altincicek et al., *J. Bacteriol.* (2001), 183(8), 2411-2416; Campos et al., *FEBS Lett.* (2001), 488 (3), 170-173).

The term "lower carotenoid biosynthetic pathway" refers to any of the following genes and gene products (including homologs and mutants thereof, whether naturally-occurring or genetically engineered) associated with the isoprenoid biosynthetic pathway, which are involved in the immediate synthesis of phytoene (whose synthesis represents the first step unique to biosynthesis of carotenoids) or subsequent reactions. These genes and gene products include the "ispA" gene (encoding geranyltransferase or farnesyl diphosphate synthase), the "ctrN" and "ctrN1" genes (encoding diapophytoene dehydrogenases), the "crtE" gene (encoding geranylgeranyl pyrophosphate synthase), the "crtX" gene (encoding zeaxanthin glucosyl transferase), the "crtY" gene (encoding lycopene cyclase), the "crtI" gene (encoding phytoene desaturase), the "crtB" gene (encoding phytoene synthase), the "crtZ" gene (encoding β-carotene hydroxylase), and the "crtO" gene (encoding a β-carotene ketolase). Additionally, the term "carotenoid biosynthetic enzyme" is an inclusive term referring to any and all of the enzymes in the present pathway including CrtE, CrtX, CrtY, CrtI, CrtB, CrtZ, and CrtO.

The term "IspA" refers to the protein encoded by the ispA gene, and whose activity catalyzes a sequence of 3 prenyltransferase reactions in which geranyl pyrophosphate (GPP), farnesyl pyrophosphate (FPP), and geranylgeranyl pyrophosphate (GGPP) are formed.

The term "CrtN1" or "CrtN, copy1" refers to copy 1 of the diapophytoene dehydrogenase enzyme encoded by crtN1 gene. The term "CrtN2" or "CrtN copy2" refers to copy 2 of the diapophytoene dehydrogenase enzyme (Crt) encoded by crtN2 gene.

The term "CrtE" refers to geranylgeranyl pyrophosphate synthase enzyme encoded by crtE gene which converts trans-trans-farnesyl diphosphate and isopentenyl diphosphate into pyrophosphate and geranylgeranyl diphosphate.

The term "CrtX" refers to the zeaxanthin glucosyl transferase enzyme encoded by the crtX gene, and which glycosolates zeaxanthin to produce zeaxanthin-β-diglucoside. The term "CrtY" refers to the lycopene cyclase enzyme encoded by the ctfY gene and which catalyzes conversion of lycopene to β-carotene.

The term "Crtl" refers to the phytoene desaturase enzyme encoded by the crtl gene and which converts phytoene into lycopene via the intermediaries of phytofluene, zeta-carotene, and neurosporene by the introduction of four double bonds.

The term "CrtB" refers to the phytoene synthase enzyme encoded by the crtB gene which catalyzes the reaction from prephytoene diphosphate to phytoene. The term "CrtZ" refers to the β-carotene hydroxylase enzyme encoded by crtZ gene which catalyzes the hydroxylation reaction from β-carotene to zeaxanthin.

The term "CrtO" refers to the β-carotene ketolase enzyme encoded by crtO gene which catalyzes conversion of β-carotene into canthaxanthin (two ketone groups) via echinenone (one ketone group) as the intermediate.

The term "HpnD" refers to putative dehydrosqualene synthase, which is thought to combine a dehydrated and a standard farnesyl-PP group to generate the $C_{30}$ molecule dehydrosqualene and is encoded by the gene hpnD.

The term "HpnE" refers to putative dehydrosqualene reductase, which is thought to reduce dehydrosqualene to generate the $C_{30}$ molecule dehydrosqualene and is encoded by the gene hpnE.

The term "HpnC" refers to squalene synthase, which combines two farnesyl-PP groups to generate the $C_{30}$ molecule squalene and is encoded by the gene hpnC.

The term "SHC" refers to squalene-hopene cyclase that converts the linear squalene molecule into the pentacyclic molecule hopene and is encoded by the gene shc (also known as hpnF). In some embodiments, the modified bacteria of the invention contains a knockout of shc, e.g., as *M. extorquens* having a shc knockout which results in elevated levels of carotenoid production (see, e.g., Example 7).

The term "carotenoid compound" is defined as a class of hydrocarbons (carotenes) and their oxygenated derivatives (xanthophylls) consisting of eight isoprenoid units joined in such a manner that the arrangement of isoprenoid units is reversed at the center of the molecule so that the two central methyl groups are in a 1,6-positional relationship and the remaining nonterminal methyl groups are in a 1,5-positional relationship. All carotenoids may be formally derived from the acyclic $C_{40}H_{56}$ structure (Formula I below), having a long central chain of conjugated double bonds, by (i) hydrogenation. (ii) dehydrogenation, (iii) cyclization, or (iv) oxidation, or any combination of these processes.

Formula I

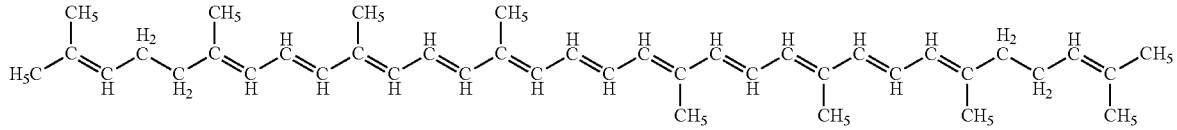

(I)

The present invention provides for the expression of genes involved in the biosynthesis of carotenoid compounds in microorganisms which are able to use single carbon substrates as a sole energy source. Such microorganisms are referred to herein as C1 metabolizers. The host microorganism may be any C1 metabolizer which has the ability to synthesize isopentenyl pyrophosphate (IPP) the precursor for many of the carotenoids. Many C1 metabolizing microorganisms are known in the art which are able to use a variety of single carbon substrates. Single carbon substrates useful in the present invention include but are not limited to methane, methanol, formaldehyde, formic acid, methylated amines (e.g., mono-, di- and tri-methyl amine), methylated thiols, and carbon dioxide. All C1 metabolizing microorganisms are generally classified as methylotrophs. Methylotrophs may be defined as any organism capable of oxidizing organic compounds which do not contain carbon-carbon bonds. A subset of methylotrophs is the methanotrophs, which have the distinctive ability to oxidize methane. Facultative methylotrophs have the ability to oxidize organic compounds which do not contain carbon-carbon bonds, but may also use other carbon substrates such as sugars and complex carbohydrates for energy and biomass. Obligate methylotrophs are those organisms which are limited to the use of organic compounds which do not contain carbon-carbon bonds for the generation of energy and obligate methanotrophs are those obligate methylotrophs that have the ability to oxidize methane.

Facultative methylotrophic bacteria are found in many environments, but are isolated most commonly from soil, landfill and waste treatment sites. Many facultative methylotrophs are members of the α, β, and γ subgroups of proteobacteria (Hanson et al., Microb. Growth 01 Compounds., [Int. Symp.], 7th (1993), 285-302. Editor(s): Murrell, J. Collin; Kelly, Don P. Publisher: Intercept, Andover, UK; Madigan et al., Brock Biology of Microorganisms, 8th edition, Prentice Hall, UpperSaddle River, N.J. (1997)). Facultative methylotrophic bacteria suitable in the present invention include but are not limited to, *Methylophilus, Methylobacillus, Methylobacterium, Hyphomicrobium, Xanthobacter, Bacillus, Paracoccus, Nocardia, Arthrobacter, Rhodopseudomonas*, and *Pseudomonas*. Preferred obligate methanotrophs are included in, but not limited to, the genera *Methylobacterium, Methylomonas, Methylobacter, Methylococcus, Methylosinus, Methylocyctis, Methylomicrobium*, and *Methanomonas*.

The ability to utilize single carbon substrates is not limited to bacteria but extends also to yeasts and fungi. A number of yeast genera are able to use single carbon substrates in addition to more complex materials as energy sources. Specific methylotrophic yeasts useful in the present invention include but are not limited to *Candida, Hansenula, Pichia, Torulopsis*, and *Rhodotorula*.

Of particular interest in the present invention are high growth facultative methylotrophs having an energetically favorable carbon flux pathway. For example, the Applicants have discovered a specific strain of methylotroph having several pathway features which make it particularly useful for carbon flux manipulation and the production of carotenoids and additional nutrients. This type of strain has served as the host in the present application and is an α-proteobacterium known as *Methylobacterium extorquens*.

The C1 metabolizing microorganisms of the present invention are ubiquitous and many have been isolated and characterized. A general scheme for isolation of these strains includes addition of an inoculum into a sealed liquid mineral salts media, containing either methane or methanol. Care must be made of the volume:gas ratio and cultures are typically incubated between 25-55° C. Typically, a variety of different methylotrophic bacteria can be isolated from a first enrichment, if it is plated or streaked onto solid media when growth is first visible. Methods for the isolation of methanotrophs are common and well known in the art (see for example Thomas D. Brock in Biotechnology: A Textbook of Industrial Microbiology, Second Edition (1989) Sinauer Associates, Inc., Sunderland, Mass.; Deshpande, Mukund V., *Appl. Biochem. Biotechnol.*, 36: 227 (1992); or Hanson, R. S. et al. The Prokaryotes: a handbook on habitats, isolation, and identification of bacteria; Springer-Verlag: Berlin, N.Y., 1981; Volume 2, Chapter 118).

It is expected that the present teaching will enable the general identification and isolation of organisms exhibiting desired characteristics. One aspect of a C1 metabolizer is that it incorporates an active Embden-Meyerhof pathway as indicated by the presence of a pyrophosphate dependent phosphofructokinase. Another key characteristic of the present high growth strain is that it is a facultative methylotroph, able to use methanol (or other C1 substrates) as a sole carbon source; of course, for optimal growth, other carbon-containing nutrients may be included, or other C1 nutrients supplemented in addition to the methanol. Methods for the isolation of methanotrophs are common and well known in the art. Similarly, pyrophosphate dependent phosphofructokinase has been well characterized in mammalian systems and assay methods have been well developed (see for example Schliselfeld et al. *Clin. Biochem.* (1996), 29(1), 79-83; Clark et al., *J. Mol. Cell. Cardiol.* (1980), 12(10), 1053-64. The contemporary microbiologist will be able to use these techniques to identify the present high growth strain.

EXEMPLIFICATION

The invention having been described, it will be further understood by reference to the following non-limiting examples.

Example 1

Directed Evolution of Methylotrophic Bacteria

Directed evolution is capable of yielding enhancement of a desired trait, such as selection for highly pigmented organisms. The technique is adapted here for the selection/evolution of *M. extorquens* overproducing astaxanthin and a number of essential amino acids. According to the present invention, one route to carotenoid production is to simply evolve cultures under the desired industrial conditions in order to improve growth rates and/or survival under the relevant environmental parameters. As this is proceeding, the visible nature of carotenoids can be used as a screen for lineages that are either losing coloration while they adapted, or those that have fortuitously become more highly pigmented. An example selection regime would be serial transfers in minimal medium containing just methanol. Upon plating cultures occasional isolates may be noted for having a "dark pink" or "reddish" colony morphology. This approach has yielded various strains with increased or altered pigmentation, as noted in Table 1 of Lee et al. (2009. Evolution. 63:2816-2830). Upon genome resequencing, the basis of the pigmentation can be revealed and combined with other developments below. Application of selection/evolution will also lead to increased methanol tolerance by culturing under ever higher concentrations beyond the ~1% tolerated now, to 5%, 10%, or higher. Experimental evolution may be carried out by serial transfers performed every 48 hours (within 1 hour) by transferring 150 μL into 9.45 mL of fresh media (a 1/64 dilution, thus permitting six generations of growth before reaching stationary phase). This provides a population size at the end of each cycle of ~$2 \times 10^9$ (9.6 mL). Populations can be maintained at 30° C. in 50 mL flasks with 225 rpm shaking. At regular intervals following the transfer of 1/64 of the population to fresh media, an appropriate dilution of the remaining culture can be plated to test for contamination, and then 750 μL of DMSO was added to the remaining liquid (~8% v/v DMSO final concentration) and duplicate vials of this mixture were preserved at −80° C. It is at the time of plating that colonies may be examined for variants with differing pigmentation. FIG. 11 in U.S. Ser. No. 61/863,701 is an image of "matchsticks" showing various levels of carotenoids in *Methylobacterium extorquens* strains: compared to the control (1), the next three (2-4) show evolved isolates, and (6) shows a hopanoid-deficient strain compared to its progenitor (5).

Directed evolution can also be utilized to select for increased production of diffusible molecules such as amino acids.

Example 2

Directed Genetic Engineering of Methylotrophic Bacteria Using Recyclable Antibiotic Marker System By combining a "feeder" strain of *E. coli* that requires a given nutrient (such as methionine, or other amino acids) with the methylotroph utilized (such as *M. extorquens*) it is possible to select for strains whose amino acid production feed their partner and allow growth of the consortia. In order to correlate production with growth advantage of that new genotype it is essential to perform these experiments in a spatially structured manner, such as on agar or agarose-containing petri dishes that contain a food source only utilizable by *E. coli* (such as glucose or lactose) but omit the addition of the nutrient that that *E. coli* mutant requires. Selection conditions involve plating the two strains together for an extended period of time (multiple days or weeks), then washing the combined cell material, vortexing, and re-plating a dilution onto fresh medium as before. In some instances it may be beneficial to combine this approach with the addition of a toxic analogue that will create direct selection for increased production to overcome the inhibitory effects of the toxic analogue.

Directed genetic engineering can be used as a strategy to increase production of carotenoids, or other desirable molecules. Two major approaches are envisioned. First, pathways which withdraw carbon to alternative products such as hopanoids, spirilloxanthin, and the addition of geranylgeranyl groups to bacteriochlorophyll. Allelic replacement constructs can be generated which contain the upstream and downstream flanks of the genes to be deleted in an allelic exchange vector such as pCM433 (Marx, C. J. *BMC Research Notes* (2008) 1:1). Through use of triparental matings such a construct can be introduced by selecting for tetracycline resistance, and then resolved by selecting for sucrose resistance (and counter-screening for tetracycline sensitivity; potential positives confirmed by PCR or sequencing). The next gene(s) to be removed can then occur in that background. The major targets—all described above—are: 1.) the genes that withdraw farnesyl diphosphate to generate hopanoids (collectively encoded by the hpnCDEF locus), 2.) those that withdraw lycopene to make spirilloxanthin (encoded by crtD, crtE and crtF), and 3.) the genes involved in decorating bacteriochlorophyll with a geranylgeranyl group (encoded by bchG and bchP). These removals can occur alone or together, and may be combined with other alterations.

Figure 3:
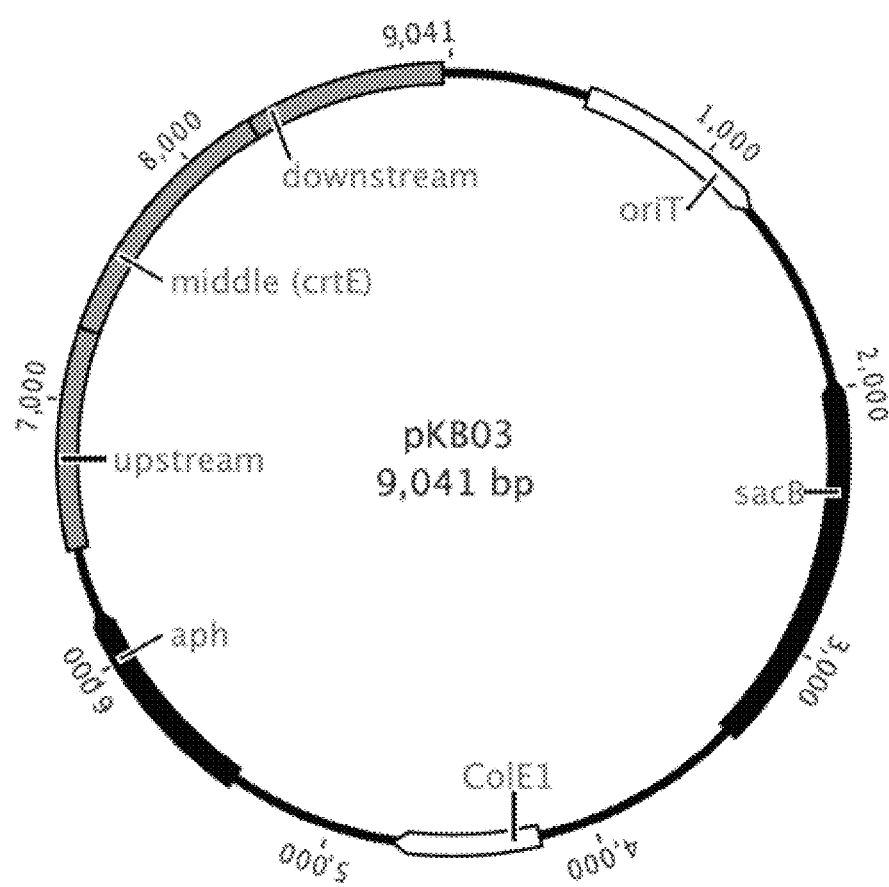
FIG. 3 shows a map of pKB03: deletion construct for cluster of crtCDF (Mext_2725-26, -28), while preserving crtE (Mext_2727), described in Example 7.

One technique to be employed will utilize recyclable antibiotic marker systems such as the cre-lox system. This will include use of the pCM157, pCM158, pCM184, pCM351 series of plasmids developed for use in *M. extorquens* (Marx, C. J. and M. E. Lidstrom *BioTechniques* (2002) 33: 1062-1067). See FIG. 4 in U.S. Ser. No. 61/863, 701, which shows a rationale for cre-lox marker recycling in *Methylobacterium* and other methylotrophs. The strategy for cre-lox recycling of antibiotic markers in *Methylobacterium* and other bacteria is illustrated in FIG. 3 of Marx and Lidstrom, 2002. BioTechniques (33:1062-1067). Cre recombinase is a site-specific recombinase from the P1 phage that catalyzes in vivo excision of DNA regions flanked by co-directional loxP recognition sites. The system used here consists of a mobilizable allelic exchange vector with a loxP-flanked antibiotic resistance cassette, pCM184 or pCM351, and an IncP plasmid that expresses the Cre recombinase, pCM157 or pCM158. We demonstrate the broad utility of this system by generating unmarked mutant strains of two phylogenetically distinct Gram-negative bacteria, *Methylobacterium extorquens* AM1 (an α-proteobacterium), and *Burkholderia fungorum* LB400 (a β-proteobacterium).

Materials and Methods

Media and Growth Conditions

*M. extorquens* AM1 strains were grown on a minimal salts medium containing carbon sources at the following levels, 0.2% citrate, 0.5% (v/v) methanol, 0.25% (wt/v) methylamine, and 0.4% (wt/v) succinate. *Escherichia coli* strains were grown on LB medium. Antibiotics were added at the following final concentrations, unless noted: 50 μg/mL ampicillin, 10 μg/mL chloramphenicol, 50 μg/mL (for *E. coli* and *M. extorquens* AM1) or 20 μg/mL (for *B. fungorum* LB400) kanamycin, 50 μg/mL rifamycin, 35 μg/mL streptomycin, and 10 μg/mL tetracycline. Chemicals were obtained from Sigma. Nutrient agar and Bacto-agar were obtained from Difco. Conjugation was performed using standard techniques.

Figure 5:
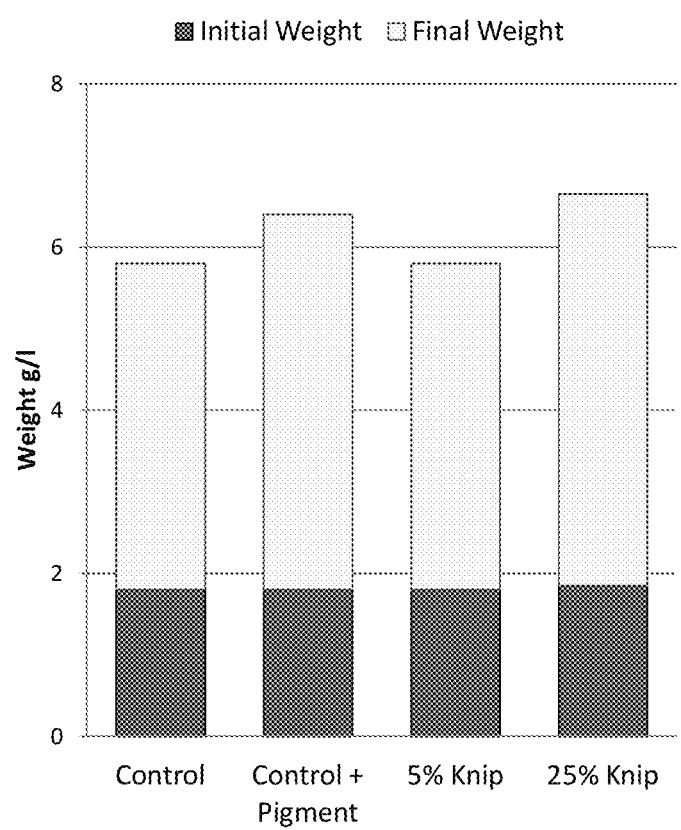
FIG. 5 shows growth of the smallmouth grunt using 4 experimental diets, as described in Example 9, which included: (1) a standard commercially available grunt diet, (2) the standard diet plus astaxanthin pigment (~80 PPM), (3) a diet containing 5% of the total feed pellet replaced by KnipBio single cell protein (KBM), and (4) a diet with 25% of the fish meal replaced by KBM (~60 PPM carotenoids).

Construction of a broad-host-range cre-lox system for antibiotic marker recycling Two allelic exchange vectors, pCM184 and pCM351 (FIG. 5 in U.S. Ser. No. 61/863,701, which shows plasmids useful for cre-lox marker recycling in *Methylobacterium* and other methylotrophs. The plasmids used to enable cre-lox recycling of antibiotic markers in *Methylobacterium* and other bacteria are illustrated in FIGS. 1 and 2 of Marx and Lidstrom, 2002. BioTechniques (33:1062-1067).), were created by inserting a loxP-bounded antibiotic resistance cassettes into a variant of the mobilizable suicide plasmid, pAYC61. The 1.3 kb HindIII fragment bearing the kanamycin resistance cassette from pUC4K was inserted into pLox1 which had been cut with XbaI and blunted, to create pCM161. In order to introduce convenient multiple cloning sites, the loxP-bounded kanamycin cassette of pCM161 was amplified with following primer pair, CM-ufkMCS, 5'-TGACGTCTAGATCTGAATTCAGCTGTACAAT-TGGTACCATGGATGCATATGGC GGCCGCA-3' (SEQ ID NO:1), and CM-dfkMCS, 5'-GACTAGTGAGCT-CACCGGT-TAACACGCGTACGTAGGGCCCGCGGTATCGATA AGCTGGATCC-3' (SEQ ID NO:2). The resulting 1.4 kb PCR product was purified and cloned into pCR2.1 (Invitrogen, Carlsbad, Calif.) to create pCM183. In order to preserve useful cloning sites, pAYC61 was cut with EcoRI and SmaI, blunted using T4 DNA polymerase, and self-ligated to produce pCM182. Finally, the 1.4 kb AatII-SpeI fragment from pCM183 containing the loxP-flanked kanamycin cassette was ligated between the AatII and XbaI sites of pCM182 to create pCM184 (GenBank accession number AY093429). A gentamycin-resistance conferring version, pCM351, was also generated. The loxP-flanked gentamycin-resistance cassette (encoded by aaaC1) was amplified from pLoxGen4 using CM-ufkMCS and CM-dfkMCS and cloned into pCR2.1 (Invitrogen, Carlsbad, Calif.) to produce pCM350. The 1.0 kb AatII/SacI fragment from pCM350 was cloned between the AatII and SacI sites of pCM184 to generate pCM351 (GenBank accession number AY093430).

Two broad-host-range cre expression vectors, pCM157 and pCM158 (FIG. 5 in U.S. Ser. No. 61/863,701), were created based upon a pair of small, mobilizable IncP plasmids. The 1.1 kb XbaI-EcoRI fragment from pJW168 was cloned between the XbaI and EcoRI sites of pCM62 to generate the tetracycline-resistance conferring cre expression plasmid pCM157. A kanamycin-resistant version, pCM158, was generated by cloning the same XbaI-EcoRI fragment from pJW168 between the XbaI and EcoRI sites of pCM66. These plasmids contain cre behind the *E. coli* lac promoter. In *M. extorquens* AM1, this promoter provides only low constitutive activity. Despite this low expression, the majority of cells obtained from the first passage onto plates lacking kanamycin are already kanamycin sensitive (data not shown).

Generation of a Δfae mutant of *M. extorquens* AM1

*M. extorquens* AM1 mutants defective for fae (encodes formaldehyde-activating enzyme) were generated using pCM184. The regions immediately flanking fae were amplified by PCR using the following primer pairs: CM-Dfae-1, 5"-CGGGTTTCGTGACCTGTTC-3" (SEQ ID NO:3), and CM-Dfae-2,5"-GTTATGCGGCCGCCATCTGCATG-GAAGCCATCCTTGTTTGC-3" (SEQ ID NO:4); and CM-Dfae-3,5"-GCTTATCGA-TACCGTCGACCTCGAGGCAGTCCTGGGCAGA-3" (SEQ ID NO:5), and CM-Dfae-4,5"-CGGG-CATCGAGCGTTTCAC-3" (SEQ ID NO:6). The purified PCR products for fae-upstream and fae-downstream were cloned into pCR2.1 to produce pCM195, and pCM196, respectively. The 0.6 kb EcoRI-NotI fragment from pCM195 was introduced between the EcoRI and NotI sites of pCM184 to produce pCM197. Subsequently, the 0.6 kb ApaI-SacI fragment from pCM196 was ligated between the ApaI and SacI sites of pCM197 to produce pCM198.

A Δfae::kan mutant of *M. extorquens* AM1 was generated by introducing pCM198 by conjugation from *E. coli* S17-1. Kanamycin-resistant transconjugants obtained on succinate medium containing rifamycin were screened for tetracycline sensitivity to identify potential null mutants. To date, we have generated over thirty different null mutant strains utilizing this system, and the frequency of double-crossover events has varied from 5% to 80% (C. J. Marx and M. E. Lidstrom, unpublished data). One such Δfae::kan mutant, CM198K.1, was chosen for further study. The plasmid pCM157 was introduced by conjugation into CM198K.1 using the helper plasmid pRK2073. Tetracycline-resistant strains were streaked for purity until the resulting strain produced only kanamycin-sensitive colonies (generally only two transfers). Subsequently, pCM157 was cured from the strain by two successive transfers on medium lacking tetracycline to produce the Δfae strain CM198.1. Analytical PCR was performed with wild-type *M. extorquens* AM1, CM198K.1, and CM198.1 for confirmation of allelic exchange, and subsequent deletion of the kanamycin cassette (data not shown). Where examined, the sequence of the analytical PCR product indicated faithful recombination between the loxP sites (data not shown).

Generation of a ΔflhA mutant of *B. fungorum* LB400

*B. fungorum* LB400 mutants defective for flhA (predicted to encode a NAD- and glutathione-dependent formaldehyde dehydrogenase) were generated using pCM184, as described above with *M. extorquens* AM1. The regions flanking flhA were amplified by PCR using the following primer pairs: CM-BfflhAuf, 5-GGTGACGGCATTGAAGCTG-3 (SEQ ID NO:7), and CM-BfflhAur, 5-CATGCATCTTTGGTCTT-CATCGTGAATG-3 (SEQ ID NO:8); and CM-BfflhAdf, 5-ACCGCGGTCGTGCTGTACTAATCC-3 (SEQ ID NO:9), and CM-BfflhAur, 5-AGAGCTCGATACCGACC-GATAGATCTC-3 (SEQ ID NO:10). The flhA upstream and downstream PCR products were cloned into pCR2.1 (Invitrogen, Carlsbad, Calif.) to produce pCM360 and pCM361, respectively. The 0.6 kb SacII-SacI downstream fragment from pCM361 was introduced between the SacII and SacI sites of pCM184 to produce pCM362. Subsequently, the 0.5 kb EcoRI-NsiI upstream fragment from pCM360 was ligated between the EcoRI and NsiI sites of pCM362 to produce pCM363.

A ΔflhA::kan mutant of *B. fungorum* LB400 was generated by introducing pCM363 by conjugation. Kanamycin-resistant transconjugants were obtained on citrate medium containing chloramphenicol (wild-type *B. fungorum* LB400 was found to be naturally resistant below 10-20 μg/mL). One tetracycline-sensitive strain representing a ΔflhA::kan mutant, CM363K.1, was chosen for further study. The plasmid pCM157 was used as described above to produce the ΔflhA strain CM363.1. Analytical PCR was performed with wild-type *B. fungorum* LB400, CM363K.1, and CM363.1 for confirmation (data not shown).

The minimal inhibitory concentration (MIC) of formaldehyde was determined by comparing the rate and extent of colony formation of wild-type *B. fungorum* LB400 to that of the flhA mutants CM363K.1 and CM363.1 on solid medium containing succinate as a growth substrate with various concentrations of formaldehyde. Formaldehyde was added to the plates immediately prior to the addition of the molten agar. Because an undetermined fraction of the formaldehyde will volatilize, the reported MIC of formaldehyde is a maximum value.

Results and Discussion

In order to test the broad-host-range cre-lox antibiotic marker recycling system, unmarked mutants were generated in *M. extorquens* AM1 (an α-proteobacterium) and *B. fungorum* LB400 (a β-proteobacterium). Analytical PCR confirmed replacement of each deleted gene with kan, and the subsequent excision of kan to produce the unmarked deletion (data not shown). The Mae mutant of *M. extorquens* AM1 grew like wild-type on succinate, but failed to grow on methanol or medium containing succinate and methanol. This mutant phenotype is in agreement with previous observations with a fae::kan mutant. The CM198.1 Mae strain can serve as a convenient host for structure-function studies that require expression of variant Fae proteins.

As a second demonstration of this broad-host-range antibiotic marker recycling system, a ΔflhA mutant of *B. fungorum* LB400 was generated. In other bacteria, the flhA gene encodes a glutathione-dependent formaldehyde dehydrogenase. This enzyme is involved in formaldehyde detoxification in *E. coli* and *Paracoccus denitrificans*, and is required for methylotrophic growth by the latter. The ΔflhA strain CM363.1 was found to be somewhat more sensitive to the presence of formaldehyde during growth on citrate than wild-type *B. fungorum* LB400, with a MIC of 0.1 mM compared to 0.2 mM for the wild-type. This finding demonstrates that the glutathione-dependent pathway is involved in formaldehyde detoxification across multiple branches of the proteobacteria.

In conclusion, this new broad-host-range cre-lox antibiotic marker recycling system offers the possibility to create unmarked mutants in a wide variety of Gram-negative bacteria. Utilization of allelic exchange with counter-selection against integrants, and an inherently unstable minimal IncP Cre expression plasmid, obviates the need for successful negative selection in the target organism, a feature of some previously developed marker recycling systems. Use of PCR to generate flanks for gene replacement allows for the facile generation of precise deletion mutants, as well as truncations through the introduction of start or stop codons in the primers, as needed. Variants of this system can be readily developed to allow the construction of chromosomal transcriptional or translational fusions (T. Strovas, C. J. Marx, and M. E. Lidstrom, unpublished data). Marker recycling systems such as ours described here offer a substantial advantage over standard allelic exchange methods due to the fact that it can be used iteratively to enable generation of unmarked strains bearing multiple genetic modifications. Our laboratory has already utilized this system to generate a *M. extorquens* AM1 strain bearing four separate mutations (C. J. Marx, L. Chistoserdova, and M. E. Lidstrom, unpublished data). Finally, engineered strains generated with these tools are more acceptable for environmental release owing to the absence of introduced antibiotic resistance markers.

Example 3

Directed Genetic Engineering of Methylotrophic Bacteria Using Alleic Exchange Vectors Another option for multiple genetic manipulations, which also avoids leaving behind undesired scars, is to use an "in-out" system (FIG. 7 in U.S. Ser. No. 61/863,701 shows rationale and plasmid useful for clean allelic exchange in *Methylobacterium* and other methylotrophs via sucrose counter selection. The strategy and plasmid used to enable antibiotic-free allelic exchange in *Methylobacterium* and other bacteria are illustrated in FIG. 1 of Marx, 2008. BMC Research Notes (1:1)). The basic idea behind these techniques is to first employ positive selection to select for single crossover integration of the entire donor vector due to recombination between a cloned region spanning the desired mutation in the vector and the corresponding chromosomal site. In the second step, negative selection is used to select for isolates that have recombined out the vector sequence. If the second recombination event excising the vector occurs on the same side of the introduced mutation as the first recombination event that introduced it onto the chromosome, the original chromosomal locus will be restored unchanged. If the second recombination event occurs on the opposite side of the introduced mutation, however, this results in excision of the original allele and the new mutation remains. As such, negative selection results in colonies with both resulting final states, as well as some percentage of false-positives that are resistant but have not excised the vector. As long as the false positives do not dominate, and the recombination rates to each side of the introduced mutation are reasonably balanced, screening of a modest collection of resulting recombinants will generate the desired unmarked mutation.

An "in-out" allelic exchange vector for generating unmarked mutations therefore must be able to be introduced into the recipient organism, be incapable of vegetative replication, and bear appropriate markers for positive and negative selection. Positive selection is generally accomplished using any number of antibiotic resistance genes, whereas comparably fewer options for negative selection generally exist. The most commonly used techniques are to use streptomycin (Sm) sensitivity, which comes as a pleiotropic effect of expressing the tetracycline (Tc) efflux pump, or sucrose-sensitivity that results from expression of levansucrase, encoded by sacB. Levansucrase activity is lethal in the presence of sucrose for most gram-negative bacteria. This paper presents a facile, broad-host-range "in-out" system based on sacB and has been specifically designed to allow facile unmarked allelic exchange in a wide variety of bacterial taxa. In order to test this system, allelic exchange has been performed at three different loci in *M. extorquens* AM1.

Results and Discussion

Construction of the "in-out" allelic exchange vector pCM433

In order to generate a facile system for marker-free allelic exchange across a wide variety of bacterial species, the loxP-flanked kanamycin (Km) resistance cassette of the broad-host-range marker-recycling vector, pCM184 was first excised and replaced with a synthetic linker that introduced three new restriction sites to the extensive multiple-cloning sites. Subsequently, a fragment from pDS132 bearing sacB and cat (encoding levansucrase and chloramphenicol (Cm) acetyltransferase, respectively) was introduced, generating pCM433 (FIG. 7 in U.S. Ser. No. 61/863,701)). It may be noted that initial attempts to were made to take advantage of the potential negative selection (Sm sensitivity) afforded by expression of the Tc efflux pump present on pCM184. Sm sensitivity was found to be enhanced in tet bearing cells, but the sensitivity was too modest to be utilized effectively for negative selection (Marx, unpublished results).

Allelic exchange at three loci in *M. extorquens* AM1

Three loci of interest in *M. extorquens* AM1 were chosen to test the utility of pCM433 for allelic exchange. These loci were hprA (encodes hydroxypyruvate reductase, a key enzyme of the serine cycle for assimilation of formaldehyde into biomass), mptG (encodes β-ribofuranosylaminobenzene 5'-phosphate synthase, the first dedicated enzyme for the synthesis of tetrahydromethanopterin, the $C_1$-carrier molecule used for this organism's formaldehyde oxidation pathway), and crtI (encodes phytoene desaturase, a necessary enzyme for carotenoid biosynthesis).

In all cases, constructs were made to convert the allele from wild-type (wt) to mutant, and the reciprocal reversion of mutant to wt. To accomplish this, both the ancestral, wt allele and the deletion (ΔhprA, ΔmptG) or insertion (crtI$^{502}$, generated by insertion of ISphoA/hah-Tc into crtI, followed by Cre-mediated excision of all but 132 bp of the IS) alleles were amplified by PCR, cloned into pCR2.1, sequenced, and then introduced into pCM433. Each of these donor plasmids were then introduced into the appropriate target strain via triparental conjugations and plated onto Tc plates (also containing Rif for counter-selection against *E. coli*). Tc$^R$ transconjugants were obtained at a frequency of $10^{-6}$ to $10^{-7}$. In some cases, even these single-crossover recombinants that contained both the wild-type and mutant alleles exhibited a phenotype. For example, the pool of single-crossover intermediates from either pCM441 (wt crtI allele) inserted into the white CM502 strain or pCM440 (defective crtI$^{502}$ allele) inserted into the pink CM501 strain each contained Tc$^R$ colonies of both colors. As such, one pink and one white isolate from the conjugation into each background were isolated (CM1263 (white) and CM1264 (pink) from CM502, and CM1265 (pink) and CM1266 (white) from CM501). A polar effect of pCM433 insertion into this site was clearly observed. Irrespective of whether the wt allele was being introduced into the mutant, or vise versa, strains with the wild-type allele upstream, proximal to the gene's promoter (as determined by PCR analysis for strains CM1264 and CM1265), were pink, carotenoid-containing colonies, whereas the other strains (CM1263 and CM1266) had the crtI$^{502}$ allele upstream of pCM433 and were white.

In order to select for recombinants that have excised the vector, suspensions of Tc$^R$ isolates were diluted and plated onto plates containing various levels of sucrose (2.5, 5, and 10% w/v). At all sucrose levels sucrose-resistant colonies were obtained at a frequency of $10^{-4}$ to $10^{-5}$. These colonies were then screened for Tc sensitivity (indicating the expected loss of the pCM433-based construct), as well as the expected mutant phenotype (inability to grow on methanol for ΔhprA and ΔmptG, white colonies (versus pink) for crtI$^{502}$). These were confirmed via PCR analysis using primers situated outside the region of the locus where recombination occurred. In the cases presented here, differences in the size of amplified products sufficed to distinguish the alleles used, but primers designed to distinguish single-nucleotide substitutions (or sequencing) have been used in subsequent studies (Chou and Marx, unpublished). Overall, a false positive rate of sucrose$^R$, Tc$^R$ strains generated here in *M. extorquens* AM1 was 26% (105/402). It should be noted, however, that the range of frequencies varied from 0% to 78% for different construct/recipient pairs. This is likely related to the rate of recombination for the flanking regions of each locus as compared to the rate of generating sucrose-resistance from other mechanisms. For all three loci, wild-type alleles were replaced by mutant alleles, and vise versa. In subsequent work, dozens of allelic exchanges including the introduction of single-nucleotide substitutions have been successfully performed utilizing this system (Chou and Marx, unpublished).

The broad-host-range vector for marker-free allelic exchange described here has several features that greatly facilitate its use in various systems. First, unlike a number of similar vectors, such as pDS132 from which much some of the construct derives, pCM433 relies upon a pUC-derived ColE1 replicon, such that it can be maintained and easily purified in high quantities (5-10 μg DNA from 1.5 mL liquid culture) in any desired *E. coli* strain. Second, pCM433 contains a polylinker containing a substantially larger number of restriction sites than comparable tools we are aware of, facilitating the introduction of cloned DNA fragments. Third, the presence of three antibiotic markers on pCM433 permits use in a wide range of organisms in which they are applicable. Finally, pCM433 maintains features typically found in other broad-host-range systems such as the presence of an IncP oriT that allows conjugation to be utilized for delivery into the recipient strain.

Materials and Methods

Media, Growth Conditions, and Genetic Techniques

*M. extorquens* AM1 strains were grown at 30° C. on agar plates with "Hypho" minimal salts medium; *E. coli* were grown at 37° C. on Luria-Bertani agar. Substrates and antibiotics were used at the following concentrations: methanol (125 mM), succinate (15 mM), sucrose (5% w/v unless otherwise stated), 50 μg/mL Ap (ampicillin), 20 μg/mL Cm, 50 μg/mL Km, 50 μg/mL Rif (rifamycin), 35 μg/mL Sm, and 10 μg/mL Tc.

Tri-parental conjugations were performed by mixing the *E. coli* strain with the donor plasmid, the *M. extorquens* AM1 recipient strain, and an *E. coli* strain with the helper plasmid pRK2073. This mixture was grown overnight on permissive Nutrient agar plates at 30° C. before introducing some of mix (either by streaking with a loop or by washing with Hypho and re-plating) onto selective medium containing an appropriate C source, Rif for counter-selection against *E. coli*, and the selective antibiotic (Tc for pCM433-based donors; neither Ap nor Cm works effectively in *M. extorquens* AM1, Marx, unpublished). Sucrose selection was accomplished by suspending a loop of a given strain in 100 μl Hypho (approximately $10^9$ mL$^{-1}$) and plating 50 μl of a $10^{-2}$ dilution of this suspension onto Hypho plates containing an appropriate C source (generally succinate) and 5% sucrose. Resulting strains were tested for Tc sensitivity, additional expected phenotypes (depending on the locus and allele being exchanged), and additionally, the chromosomal organization of all strains constructed was confirmed through PCR analysis. DNA concentrations were determined using a ND-1000 spectrophotometer (NanoDrop).

Construction of Plasmids and Generation of Strains

In order to generate the allelic exchange vector pCM433, the Km resistance cassette of pCM184 was excised with NdeI and SacII, and the remaining 5.4 kb vector backbone was ligated together with a synthetic linker designed to introduce three additional, unique cloning sites into the final vector (PstI, XhoI, and NotI). The linker was formed by boiling, and then slowly re-annealing at room temperature, a mixture of two oligos, CM-link1f (tatgctgcagctcgagcggccgc (SEQ ID NO:47) and CM-link1r (ggccgctcgagctgcagca (SEQ ID NO:48)), which were designed to have complementary overhangs to NdeI and SacII. The resulting plasmid, pCM432, was then transformed into the dam dcm *E. coli* strain, C2925H (ara-14 leuB6 fhuA31 lacY1 tsx78 glnV44 galK2 galT22 mcrA dcm-6 hisG4 rfbD 1 R(zgb210::Tn10) Tc$^S$ endA 1 rspL 136 (Sm$^R$) dam 13:: Tn9 (Cm$^R$) xylA-5 mtl-1 thi-1 mcrB1 hsdR2, New England Biolabs), enabling digestion at an otherwise methylated, and therefore blocked, MscI site. The 2.7 kb XbaI-XmaI fragment of pDS132 containing sacB and cat was then purified, blunted with Klenow enzyme, and ligated with the MscI-digested pCM432 vector to generate pCM433 (see FIG. 7 in U.S. Ser. No. 61/863,701). A construct with the sacB-cat fragment in the opposite orientation, pCM433r, was also obtained.

A series of constructs and strains were generated in order to test the ability of pCM433 to enable unmarked allelic exchange at three distinct loci in the *M. extorquens* AM1 chromosome. Donor constructs for allelic exchange at the mptG locus were generated by first amplifying a region including mptG from CM501 (an isolate of wild-type, Rif$^R$ *M. extorquens* AM1), or the corresponding region from the ΔmptG strain, CM508 (an isolate of CM253.1), each of which were ligated into pCR2.1 (Invitrogen) to generate pCM411 and pCM424, respectively. These PCR-amplified inserts (and all other alleles described below that were cloned into pCR2.1) were sequenced to confirm no PCR errors were introduced during amplification. The 2.1 kb ApaI-BamHI fragment of pCM411 containing the mptG region was then introduced into pCM433 that had been digested with ApaI and BglII, resulting in the donor vector pCM436. Similarly, the 1.3 kb SacI-XhoI fragment of pCM438 with the ΔhprA region was cloned into the same sites of pCM433 to generate the donor vector pCM439. This allowed the use of pCM436 (containing the wild-type mptG allele) to reverse the lesion found in CM508, while pCM437 (ΔmptG allele) was introduced into CM501 to do the opposite, generating the deletion in a single step.

Similarly, donor constructs for allelic exchange at the crtI locus were generated by first amplifying a region including crtI (encodes phytoene desaturase) from the pink CM501 strain, or the corresponding region from the white crtI:: ISphoA/hah (i.e., crtI$^{502}$) strain, CM502 (an isolate of AM1-W). These fragments were ligated into pCR2.1 (Invitrogen) to generate pCM417 and pCM426, respectively. The 1.6 kb BamHI-NsiI fragment of pCM411 containing the crtI region was then introduced into pCM433 that had been digested with BglII and NsiI, resulting in the donor vector pCM440. Similarly, the 1.7 kb BamHI-NotI fragment of pCM426 with the crtI$^{502}$ region was cloned between the BglII and NotI sites of pCM433 to generate the donor vector pCM441. This allowed the use of pCM440 (containing the wild-type crtI allele) to reverse the lesion found in CM502, while pCM441 (crtI$^{502}$ allele) was introduced into CM501 to do the opposite, generating the insertion allele.

Finally, for the third locus, hprA, an antibiotic-resistance free deletion strain was generated initially using the previously developed cre-lox system. In contrast to the system described here using pCM433, the process to generate the ΔhprA strain was substantially more involved (and resulted in leaving behind a loxP scar). First, the regions upstream and downstream of hprA, were amplified separately and cloned into pCR2.1 (Invitrogen) to generate pCM428 and pCM429, respectively. The 0.5 kb upstream region was then excised from pCM428 using BglII and NotI and ligated into the same sites of pCM184 to generate pCM430. Into this plasmid, the 0.6 kb ApaI-SacI fragment from pCM429 was cloned into the same sites to generate the donor plasmid pCM431. As previously described, this plasmid was introduced into both the wild-type (pink) *M. extorquens* AM1 strain, CM501, as well as the otherwise isogenic white strain with a crtI$^{502}$ allele, CM502, leading to the isolation of the hprA::kan strains CM1122 and CM1123, respectively. pCM157 (expressing Cre recombinase) was introduced into these two strains to catalyze the excision of the kan cassette, and was subsequently cured, ultimately resulting in the antibiotic-resistance free ΔhprA strains CM1203 and CM1204 used below.

Donor constructs for allelic exchange of the hprA locus were generated by first amplifying a region including hprA from CM501, or the corresponding region from the ΔhprA strain generated above, CM1203. Ligation of these fragments into pCR2.1 (Invitrogen) generated pCM434 and pCM438, respectively. The 2.2 kb ApaI-BamHI fragment of pCM434 containing the hprA region was introduced into pCM433 that had been digested with ApaI and BglII, resulting in the donor vector pCM434. Similarly, the 1.3 kb SpeI-NsiI fragment of pCM438 with the ΔhprA region was cloned between the XbaI and NsiI sites of pCM433 to generate the donor vector pCM439. This allowed the use of pCM434 (containing the wild-type hprA allele) to reverse the lesion found in CM1203, while pCM439 (ΔhprA allele) was introduced into CM501 to do the opposite, generating the deletion in a single step.

Example 4

Figure 4:
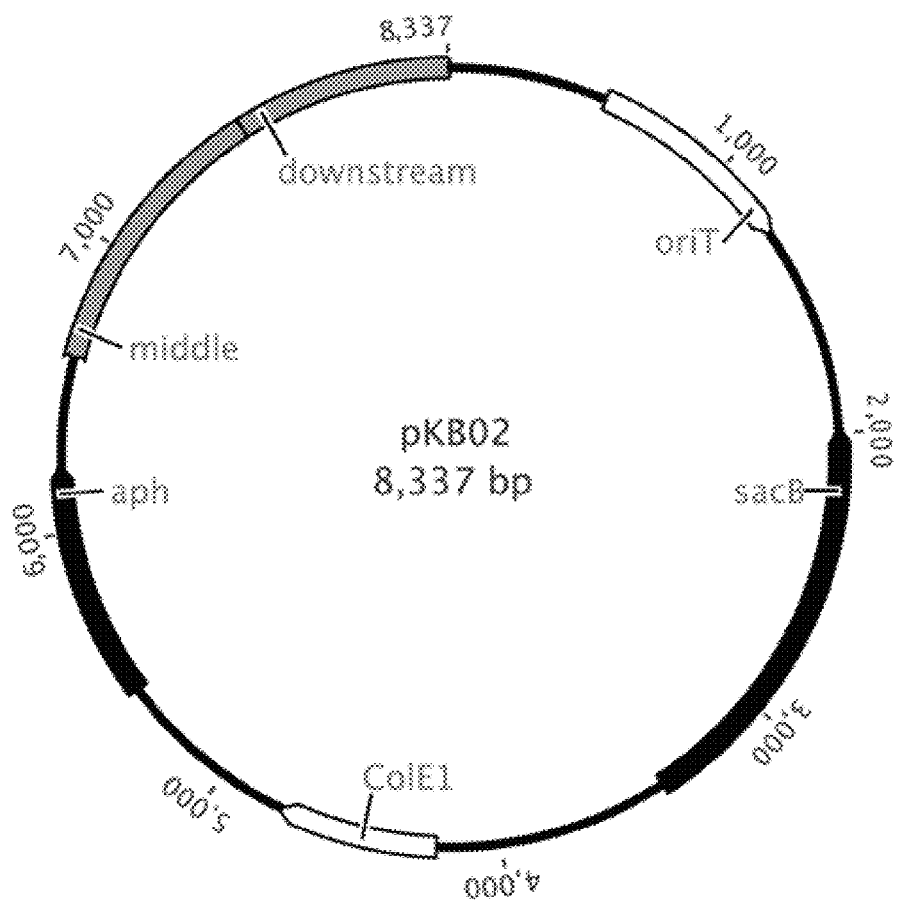
FIG. 4 shows a map of pKB02: deletion construct for crtF (Mext_2728), described in Example 7.

Directed Genetic Engineering of Methylotrophic Bacteria Using Recyclable Antibiotic Marker System Over the past few years, the genetic "toolkit" available for use with *Methylobacterium extorquens* AM1 has expanded significantly. The *Methylobacterium* organisms selected for genetic modification in the present invention can be engineered using, for example, small IncP vectors including pCM62 (FIG. 3 in U.S. Ser. No. 61/863,701 shows plasmids useful for cloning in *Methylobacterium* and other methylotrophs. The base plasmids for cloning and expression in *Methylobacterium* and other bacteria are shown in FIGS. 2 and 4 of Marx and Lidstrom, 2001. Microbiology (147: 2065-2075)), pCM66, or pHC41 for cloning (Marx, C. J. and M. E. Lidstrom Microbiology (2001) 147: 2065-2075; Chou, H.-H. et al. *PLoS Genetics* (2009) 5: e1000652). Genetic modifications will also take advantage of freely replicating expression plasmids such as pCM80 (see FIG. 3 in U.S. Ser. No. 61/863,701), pCM160, pHC90, or pHC91 (Marx, C. J. and M. E. Lidstrom *Microbiology* (2001) 147: 2065-2075; Chou, H.-H. et al. *PLoS Genetics* (2009) 5: e1000652). Other plasmids have the ability to respond to levels of inducing molecules such as cumate or anhydrotetracycline. These include pHC115, pLC 290, pLC291 (Chou, H.-H. et al. *PLoS Genetics* (2009) 5: el 000652; Chubiz, L. M. et al. *BMC Research Notes* (2013) 6: 183). In certain embodiments, genetic modifications will utilize expression systems introduced directly into a chromosomal locus. These may include pCM168, pCM172, and pHC01 plasmids developed for *M. extorquens* AM1 (Marx, C. J. and M. E. Lidstrom Microbiology (2001) 147: 2065-2075; Lee, M.-C. et al. *Evolution* (2009) 63: 2813-2830).

Figure 6:
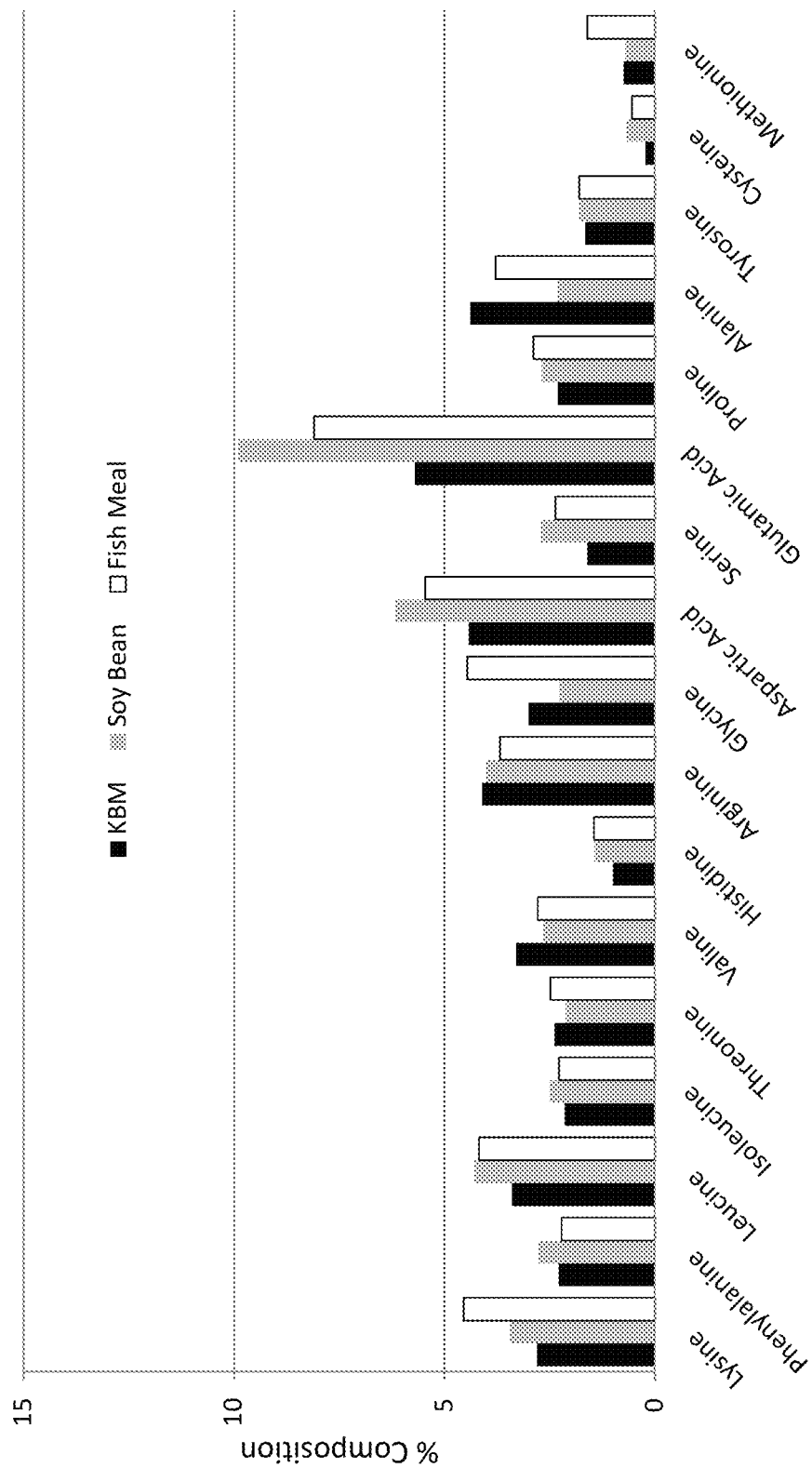
FIG. 6 shows results of an amino acid profile analysis for the KBM feed described in Example 9.

FIG. 6 in U.S. Ser. No. 61/863,701 shows plasmids useful for insertional expression from a chromosomal locus in *M. extorquens* AM1. The plasmids used for chromosomal cloning and expression in *Methylobacterium extorquens* are illustrated in FIG. 2 of Marx and Lidstrom, 2004. Microbiology (150:9-19). As described in Marx, C. J. et al. *Microbiology* (2004), 150: 9-19, an insertional expression system has been developed that allows expression of genes from a stable, unmarked chromosomal locus. This system has been used to better understand the role of the tetrahydrofolate ($H_4F$) pathway in methylotrophy. Previously, it has not been possible to generate null mutants lacking either mtdA (encoding an NADP-dependent methylene-$H_4F$/methylene-tetrahydromethanopterin dehydrogenase) or fch (encoding methenyl-H$_4$F cyclohydrolase). An unmarked strain was generated that expressed the analogous folD gene (encoding a bifunctional NADP-dependent methylene-H$_4$F dehydrogenase/methenyl-H$_4$F cyclohydrolase) from *Methylobacterium chloromethanicum* CM4$^T$. In this strain, null mutants could be obtained that grew normally on multicarbon substrates but were defective for growth on C$_1$ substrates. Additionally, null mutants of mtdA and/or fch could also be generated in the wild-type by supplementing the succinate medium with formate. These strains were unable to grow on C$_1$ compounds but were not methanol-sensitive. These approaches have demonstrated that the apparent essentiality of mtdA and fch is due to the need for formyl-H$_4$F for biosynthesis of purines and other compounds, and have provided clear genetic evidence that the H$_4$F pathway is required for methylotrophy.

Directed genetic engineering can also be used to increase expression of biosynthetic pathways needed to generate lycopene. This can be accomplished by cloning the region flanking the native promoter upstream of such a gene (or operon) and replacing the promoter with one of moderate to high strength. These include the strong promoter driving expression of the methanol dehydrogenase operon (P$_{mxaF}$) or the rhizobiaphage promoter (P$_R$) (Chubiz, L. M. et al. *BMC Research Notes* (2013) 6: 183). As described above, these genes included dxs, dxr, and ispDEF that lead to isopentyl diphosphate, and idi, ispA, crtE, crtB, and ctrI to generate lycopene. These manipulations can occur alone or together, and may be combined with other alterations.

Directed genetic engineering can be used to introduce novel enzymatic capacities needed to synthesize novel biomolecules, such as astaxanthin. This can be accomplished by cloning the necessary genes in their native, codon optimized, or otherwise manipulated version. These enzymes can be introduced into the desired host with a replicating plasmid-based system, such as pCM80, pCM160, pHC90, pHC91, pHC115, pLC290, or pLC291. Alternatively, for stable maintenance in the absence of selection they can be introduced onto the chromosome using systems described above, including pCM168, pCM172, and pHC01 developed for *M. extorquens*. Just three enzymes are required to extend from lycopene to astaxanthin: lycopene cyclase, encoded by crtY, β-carotene ketolase, encoded by crtW, and β-carotene hydroxylase, encoded by crtZ. These can be expressed from individual loci or fused into a synthetic operon. In some embodiments crtY and crtW will originate from the closely related *Bradyrhizobium* sp. ORS 278. In some embodiments crtZ will originate from the fellow α-proteobacterium *Brevundimonas* sp. SD212.

Wild-type *M. extorquens* or an available high pigment strain may be grown on methanol in order to serve as a feedstock for fish. Methanol levels added in fed-batch method can be maximized, within the constraints of the other nutrients present in the medium. Total additions of methanol to 5-10% v/v are desirable. To enable this, additional nitrogen may need to be added in the form of ammonium sulfate or ammonium chloride. Given the tendency for methanol growth to lower the pH of the medium, bases such as sodium bicarbonate or sodium hydroxide can be added to maintain pH close to initial levels (generally pH 6.2 to 7). The final optical density of the culture can be determined via dilutions analyzed spectrophotometrically.

Example 5

Inducible Expression Vectors for use in Methylotrophic Bacteria

To date, only one regulated expression system has been demonstrated to be functional in *M. extorquens*. Choi and coworkers constructed an inducible expression system utilizing the cumate responsive transcriptional repressor, CymR, from *Pseudomonas putida* F1 and the strong P$_{mxaF}$ promoter that drives the expression of methanol dehydrogenase in *M. extorquens*. This hybrid system has been modified and utilized to test the fitness consequences of gene expression levels of different formaldehyde oxidation enzymes in *Methylobacterium*. While functional, this promoter-operator pairs are extremely "leaky", wherein the basal level of expression in non-inducing conditions is quite high. This limitation makes heterologous gene expression exceedingly difficult, and hampers the exploration of conditionally null phenotypes.

Building on these previous findings, we have employed an additional transcriptional repressor, TetR, from the transposon Tn 10. As the foundational member of the TetR-family of DNA binding proteins, of which CymR is also a member, TetR has been extensively studied yielding much data on ligand binding, DNA binding kinetics, and operator site specificity. In the absence of inducer, TetR and CymR bind tightly to their respective operator sites (see FIG. 8 in U.S. Ser. No. 61/863,701 shows cumate- and anhydrotetracycline-regulated promoter systems for use in *Methylobacterium*. The plasmids used to for regulated expression in *Methylobacterium* are illustrated in FIG. 1 of Chubiz et al., 2013. BMC Research Notes (6:183).), thereby inhibiting transcriptional initiation by RNA polymerase. Upon binding of ligands such as tetracycline or anhydrotetracycline (a high-affinity ligand) in the case of TetR, or cumate (p-isopropyl benzoate) with CymR, the affinity of TetR and CymR for their respective operator sites is nearly abolished, allowing for transcription initiation to proceed. Exploiting these characteristics, numerous studies have modified existing expression systems to behave in a dose-dependent manner. In fact, TetR and related transcriptional repressors have found use in numerous synthetic biology applications in bacteria, archaea, and eukaryotes.

Here we describe the construction of two McP-based, inducible expression vectors for use in *M. extorquens*, and possibly numerous other proteobacteria with minor modification. The novelty of these vectors lies in their use of two separate transcriptional repressors, TetR and CymR, along with a strong promoter from the rhizobial phage 16-3. We demonstrate the utility of these vectors by showing that i) induction is dose-dependent, ii) induction is continuous through time, and iii) the regulatory range of both systems exceeds those currently available for *M. extorquens*. Collectively, these results supply researchers investigating *M. extorquens*, and likely numerous other proteobacteria, with two alternative systems to express genes in traditional and synthetic biology applications.

Findings

Promoter Design and Rationale

During the process of selecting an appropriate promoter, we desired that the promoter i) be sufficiently active in *M. extorquens* and ii) not be subject to regulation by native transcription factors. Based on these two criteria, a natural source for such a promoter was from bacteriophage. Many bacteriophage promoters have a wide host range and often have strong, constitutive activity in the absence of their transcriptional control mechanisms. However, numerous well characterized coliphage-derived promoters such as $\lambda P_L$, $\lambda P_R$, T5 $P_N$ 25, T7 $P_{A1}$ are weakly active or inactive in *M. extorquens*. To this end, we looked to other bacteriophage promoters that have been shown to be active in α-proteobacteria. Based on this metric, we explored the use of 5 promoters from the control region of the rhizobial phage 16-3 ($P_L$ and $P_R$). Phage 16-3 has been extensively examined with physiological and biochemical studies in both its host, the α-proteobacterium *Sinorhizobium meliloti*, and *Escherichia coli*, suggesting that $P_L$ and $P_R$ may be functional in a variety of hosts. Additionally, the only transcriptional regulator known to interact with $P_L$ and $P_R$ is the 16-3 C repressor.

In a set of exploratory experiments, we found that $P_R$ was active in *M. extorquens* (data not shown). As we desired to construct inducible systems, we focused attention to engineering $P_R$ derivatives containing operator sites for the CymR and TetR regulators (FIG. 8 in U.S. Ser. No. 61/863,701 shows cumate- and anhydrotetracycline-regulated promoter systems for use in *Methylobacterium*). The plasmids used to for regulated expression in *Methylobacterium* are illustrated in FIG. 1 of Chubiz et al., 2013. BMC Research Notes (6:183).). The resulting hybrid promoters, $P_{R/cmtO}$ and $P_{R/tetO}$, were found to produce the widest regulatory range without interfering with P R promoter activity. Interestingly, we found that placing the operators, specifically tetO, throughout other regions of the promoter resulted in either loss of promoter repression or activity (data not shown). This was a somewhat surprising result given the flexibility of many other phage-derived systems to be manipulated with multiple repressor and activator operator sites. Collectively, these findings allowed us to engineer two inducible promoters with similar maximal activity (FIG. 9 in U.S. Ser. No. 61/863,701 shows titratability of the regulated promoter systems shown in FIG. 7). The response of expression from pLC290 and pLC291 with addition of inducer in *Methylobacterium* are shown in FIG. 2 of Chubiz et al., 2013. BMC Research Notes (6:183).).

Activation of $P_{R/cmtO}$ and $P_{R/tetO}$ is Dose-Dependent

A desirable property for regulated expression systems is for levels of gene expression from the promoter to be proportional to the concentration of inducer. In order to explore the range of induction of $P_{R/cmtO}$ and $P_{R/tetO}$, the promoters along with their respective regulatory proteins were introduced onto broad-host-range plasmids (IncP compatibility group) to create the expression vectors pLC290 and pLC291 (FIG. 8 in U.S. Ser. No. 61/863,701). Since previous studies have demonstrated mCherry to be a sensitive measure of gene expression in *M. extorquens*, we decided to use mCherry fluorescence as a metric of promoter activity. We placed the red-fluorescent protein variant mCherry under the control of each promoter in pLC290 and pLC291 and introduced the resulting vectors (pJP18T and pJP22T) into *M. extorquens*. To induce expression from $P_{R/cmtO}$ and $P_{R/tetO}$, we supplied varied concentrations of cumate (Q) and anhydrotetracycline (aTc), respectively, to *M. extorquens* cultures.

In general, both promoters were found to be responsive to concentrations of Q and aTc that were in agreement with previous studies in *M. extorquens* or other organisms. The $P_{R/cmtO}$ promoter was observed to respond to a range of 0.1 to 5 µg/mL (0.6 to 30 µM) of Q and the $P_{R/tetO}$ promoter from 0.1 to 25 ng/mL (0.2 nM to 50 nM) aTc. Interestingly, the induction profile of $P_{R/cmtO}$ increased in a log-linear fashion over the entire concentration range, whereas $P_{R/tetO}$ was observed to have a much more concave profile. In terms of regulatory range, $P_{R/cmtO}$ and $P_{R/tetO}$ were observed to have 10-fold and 30-fold induction, respectively, with both promoters having the same maximum absolute levels of expression (FIG. 9 in U.S. Ser. No. 61/863,701). Importantly, the basal level of expression from $P_{R/cmtO}$ was found to be approximately 3-fold higher than that of $P_{R/tetO}$. Taken together, these data suggest that while $P_{R/cmtO}$ may be more tunable, $P_{R/tetO}$ serves as a superior expression system for genes requiring tight repression, such as cytotoxic proteins. Also, we found that there was minimal crosstalk between the CymR and TetR ligand specificity or promoter binding indicating these systems would work independent of one another (pJP18T: 4.6 Uninduced/4.2 with aTc; pJP22T: 1.0 Uninduced/1.1 with Q; Grown in succinate).

Comparing the levels of gene expression and regulatory range of $P_{R/cmtO}$ and $P_{R/tetO}$ to the cumate inducible $P_{mxaF}$ promoter previously reported, we found that in *M. extorquens* these promoters achieve 33% of the maximal activity of $P_{mxaF}$ (the strongest known *Methylobacterium* promoter) and provide a greater degree of repression. Specifically, a cumate-inducible $P_{mxaF}$ mCherry expression vector, pHC115m, yielded relative fluorescence values of 15.6±1.5 (uninduced) to 157.1±3.7 (induced). While this 10-fold regulatory range was similar to $P_{R/cmtO}$, the minimal and maximal expression from $P_{R/cmtO}$ were both 3-fold lower. By comparison, $P_{R/tetO}$, with a 30-fold regulatory range, was able to repress expression 8-fold lower than the $P_{mxaF}$ system with only a 3-fold difference in maximum expression. Collectively, these results demonstrate that both $P_{R/cmtO}$ and $P_{R/tetO}$ provide improvement over previously explored systems. However, we do note that $P_{mxaF}$ may remain a superior promoter in cases when high-level protein over-expression is desired. Importantly, these hybrid promoters allow for more relevant exploration of cellular physiology as their expression levels and ranges fall well within or above native promoters in *M. extorquens*.

Maximal Activation of $P_{R/cmtO}$ and $P_{P/tetO}$ is Substrate Dependent

An issue with many expression systems designed with host-derived promoters is the possibility of interactions with native transcription factors. Specifically, the P mxaF promoter is known to be more highly active in cells grown on methanol as opposed to succinate. To explore this possibility, with respect to $P_{R/cmtO}$ and $P_{R/tetO}$, we cultured *M. extorquens* harboring pJP18T and pJP22T in media with either methanol or succinate as the sole carbon source. We found that succinate grown cells possessed a nearly 2-fold increase in maximal gene expression, compared to methanol grown cells; effectively, the opposite behavior seen with $P_{mxaF}$. We suspect that this disparity in maximal expression may be due to an external factor, such as different plasmid copy numbers, between methanol and succinate growth. Previously reported XylE and β-galactosidase promoter probe vectors used in *M. extorquens*, such as pCM130 and pCM132 (plasmids with the same back-bone as pLC290 and pLC291), exhibit between 2- and 3-fold increases in background activity during succinate versus methanol growth. As pCM130 and pCM132 possess no promoter sequences upstream of their reporter genes, the only likely variation that might exist is in plasmid copy number. Comparing these findings to our own, where $P_{R/cmtO}$ and $P_{R/tetO}$ contain no host-related transcription factor binding sites, we see similar fold changes in maximal expression suggesting that a similar mechanism may be affecting these expression systems. Taken together, these data indicate that single-copy or chromosomally integrated systems be used in situations where uniform expression is desired across substrates.

Induction of $P_{R/cmtO}$ and $P_{R/tetO}$ is Continuous

A problematic feature of many expression systems, particularly those associated with metabolic pathways, is that gene expression can exhibit phenotypic heterogeneity throughout the population of cells, such as an on-off, switch-like behavior. To explore this possibility, we grew M. extorquens strains bearing the mCherry expression vectors pJP18T and pJP22T to mid-log phase, induced cultures with either Q or aTc, and measured the time course of individual-cell fluorescence by flow cytometry. We found that over 8 hours of induction the induced populations activated transcription in a uniform, continuous manner (FIG. 10 in U.S. Ser. No. 61/863,701 shows unimodal expression during an induction time-course for each of the regulated promoter systems shown in FIG. 7 of U.S. Ser. No. 61/863,701). The time-course of smooth, non-bimodal regulation of expression from pLC290 and pLC291 in Methylobacterium are shown in FIG. 3 of Chubiz et al., 2013. BMC Research Notes (6:183).). Though we did observe residual uninduced cells, we suspect this may be due to debris introduced by our cell fixing method or possibly cells losing mCherry due to costly over-expression. These data demonstrate the utility of the $P_{R/cmtO}$ and $P_{R/tetO}$ expression systems in studying aspects of cellular physiology requiring uniform gene expression.

Complementation and Conditional Null Phenotypes Using $P_{R/tetO}$ Constructs

To examine the utility of these vectors for studying M. extorquens physiology, we complemented a gene encoding a key enzyme in methanol metabolism using the $P_{R/tetO}$-based plasmid pLC291. We chose to use utilize $P_{R/tetO}$ due to the tight induction properties we have observed using an mCherry reporter (FIG. 8 in U.S. Ser. No. 61/863,701). The product of ftfL (formate-tetrahydrofolate ligase) is required for the assimilation of formate into biomass during one-carbon metabolism. A disruption in ftfL results in a methanol minus growth phenotype. By complementing a ftfL knock-outs using ftfL-expressing vectors under the control of $P_{R/tetO}$, in the presence of aTc, we found that we could fully restore growth on methanol. Importantly, in the absence of aTc, we observed that we were able to produce a complete null phenotype for ftfL. To date, no expression system for M. extorquens has been capable of producing conditional null phenotypes. These results demonstrate the utility of $P_{R/tetO}$ to study M. extorquens physiology and generate conditional null mutants regulated by aTc.

To date, only a handful of expression systems exist for bacterial models outside E. coli and other closely related γ-proteobacteria. In an effort to expand the genetic toolkit available to researchers working with M. extorquens, and presumably other proteobacteria, we have constructed a set of two inducible expression vectors that utilize the CymR and TetR (cumate and tetracycline repressors) in conjunction with the strong PR promoter from phage 16-3. The pLC290 and pLC291 vectors were found to provide uniform, high-level expression in M. extorquens over a wide range of inducer concentrations. Importantly, compared to the only existing inducible system for M. extorquens, we found that $P_{R/cmtO}$ and $P_{R/tetO}$ have 3 and 8-fold increases in repression, respectively. This provides a significant improvement in the ability to explore M. extorquens cellular physiology. Further, as these promoters operate orthogonally to one another, we believe these expression systems will easily work in concert within a single strain to allow complex genetic engineering in a wider range of bacteria. For these reasons, we believe these vectors and promoter systems will be of great use to the bacteriological community in many research and industrial settings.

Materials and Methods

Bacterial Strains, Medium, and Growth Conditions

All bacterial strains used in this work are derivatives of Escherichia coli NEB10β (New England Biolabs), E. coli LC100 (F⁻rph-1 ilvG attλ::[spcR lacI$^Q$ tetR]), Methylobacterium extorquens PA1 strain CM2730 (Δ ceIABCD) or M. extorquens AM1. Growth of all strains, except E. coli, was performed in modified 'Hypho' minimal medium as described by Chou and coworkers, with succinate at 5 mM or methanol at 20 mM. E. coli strains were cultured in Luria-Bertani broth as described by Miller or nutrient broth. Media was supplemented with kanamycin at 50 µg/mL or ampicillin at 100 µg/mL to select for the presence of all plasmids. Inducers anhydrotetracycline (aTc) and cumate-KOH (Q) were supplied at 25 ng/mL or 5 µg/mL from aqueous stocks, respectively, unless otherwise indicated. Growth and gene expression experiments were performed at 30° C. using an automated growth system described by Delaney and coworkers.

Plasmid and Strain Construction

Promoter designs were initially constructed and subsequently mutated in a pBluescript(SK−) (Stratagene) backbone. Synthetic oligonucleotides CAACAACTTATAC-CATGGCCTACAAAAAGGCAAACAATGGTACTTGAC GACTC ATCACAA (SEQ ID NO:11) and GTCCGTTCGT-TACAATCTACAACTACAATTGTTGTGATGAGTCGT-CAAGTACC ATTG (SEQ ID NO:12) containing the sequence for a 91 nt region encoding the PR promoter from the rhizobial phage 16-3. The oligonucleotides were annealed to form a 91 bp dsDNA fragment, followed by PCR amplification with primers ATAGGGCCC-CAACAACTTATACCATGGCCTAC (SEQ ID NO:13) and ATAGGTACCGTCCGTTCGTTACAATCTACAAC (SEQ ID NO:14) to introduce PspOMI and KpnI restriction sites. The resulting fragment was digested with PspOMI and KpnI and cloned into the respective sites in pBluescript(SK−) to form pLC265. TetR and CymR opera-for sites (tetO and cmtO), were introduced at the distal end of PR in pLC265 using enzymatic inverse PCR (EI-PCR) using primers ATACGTCTCATCCCTATCAGTGATAGAGAGTTGTA-GATTGTAACGAACGGAC (SEQ ID NO:15), ATACGTCTCAGGGACGTCAAGTACCATTGTTTGCC (SEQ ID NO:16), ATACGTCTCAACAAACA-GACAATCTGGTCTGTTTGTGGTACCCAATTCGCCCT AG (SEQ ID NO:17), and ATACGTCTCATTGTTTA-CAATCTACAACTACAATTGTTGTG (SEQ ID NO:18) followed by BsmBI digestion and ligation to generate plasmids pLC271 (PR/tetO containing) and pLC277 (PR/cmtO containing).

The subsequent broad-host-range vectors were constructed using the expression vector pHC115 as a template. A DNA region encoding Tn10 tetR was PCR amplified from LC100 using primers ATAGCTAGCAGGGAGA-GACCCCGAATGATGTCTAGATTAGA-TAAAAGTAAAGT G (SEQ ID NO:19) and ATAGGGCCCTTAAGACCCACTTTCACATTTAAG (SEQ ID NO:20) containing NheI and PspOMI restriction sites. The resulting product was digested and ligated into the NheI and PspOMI sites of pHC115, thereby replacing the cymR coding region with tetR to form pLC261. From pHC115 and pLC261, the PmxaF region was excised with PspOMI and KpnI and replaced with subcloned PR/cmtO and PR/tetO fragments from pLC277 and pLC271. To the resulting plasmids, a trrnB terminator was PCR amplified from pHC01 using primers ACGCGAAATT-CAAGCGCTAGGGC-CAAGTTGGGTAACGCCAGGGTTTTCCC (SEQ ID NO:21) or ATGTGAAAGTGGGTCTTAAGGGC-CAAGTTGG (SEQ ID NO:22) (Chubiz et al. *BMC Research Notes* (2013), 6:183) GTAACGCCAGGGTTTTCCC (SEQ ID NO:23) and TGTAGGCCATGGTATAAGTTGTTGG-GATGCAAAAACGAGGCTAGTTTACC (SEQ ID NO:24) and cloned into the PspOMI site, using the method of Gibson and coworkers, to reduce transcriptional read-through into the PR/cmtO and PR/tetO promoter regions. Likewise a more comprehensive multiple cloning site was introduced into the KpnI and EcoRI sites using annealed synthetic oligonucleotides GATAGGTACCTCTAGAA-GATCTACGCGTACTAGTGCATGCGAGCTCACCGGT GATTCATAG (SEQ ID NO:25) and CTATGAATT-CACCGGTGAGCTCGCATGCACTAGTACGCGTA-GATCTTCTAGAG GACCTATC (SEQ ID NO:26) to produce the final expression vectors pLC290 and pLC291. The mCherry expression vectors pJP18T and pJP22T were created by subcloning a KpnI and EcoRI digestion product containing mCherry from pHC115m into the corresponding sites in pLC290 and pLC291, respectively. The vectors pLC290 (GenBank Accession KC296704) and pLC291 (Gen Bank Accession KC296705) are publically available.

Unmarked ftfL knockouts were generated by transforming the Cre-recombinase expression plasmid pCM157 into *M. extorquens* AM1 derivatives CM216K.1 generating strain CM2336 (ΔftfL::loxP). The ftfL complementation vector was generated by subcloning a KpnI and EcoRI digestion product of a pHC115-based ftfL plasmid (SMC unpublished) into the corresponding sites of pLC291, creating plasmids pSC54. The vector, pSC54, was introduced into CM2336 via triparental mating using the helper plasmid pRK2073, to produce strains CM4103 (ΔftfL::loxP/pSC54). Complementation was performed by inoculation of succinate grown CM4103 into methanol minimal medium containing 0 µg/mL or 20 µg/mL aTc.

Fluorescence-Based Expression Assays

Assays to measure levels of mCherry protein expression were performed as follows. For dose-dependent response curves, *M. extorquens* strains harboring pJP18T or pJP22T were grown to saturation in 10 mL of Hypho-succinate medium. These cultures were then diluted 1:200 in fresh medium, followed by 630 µL aliquots being dispensed to clear, flat-bottom, 48-well microtiter plates (Costar). Cultures were grown for 4 hours on a plate shaking tower (Caliper) at 150 rpm in a 30° C. humidified room. After 4 hours of growth, 10 µl of fresh medium containing Q or aTc was added to supply Q and aTc at desired concentrations. Cultures were allowed to continue growth for an additional 24 hours prior to fluorescence (excitation 587 nm/emission 610 nm) and optical density (600 nm) measurements made using a Tecan Safire2 plate reader. Relative fluorescence values reported are: Relative fluorescence (A.U.)=RFU/$OD_{600}*10^{-3}$.

Dynamic expression assays were conducted under similar conditions as above with the following exceptions. Cells (200 µL of culture) were harvested after induction at 0, 2, 4, 6, 8, and 24 hrs. Culture samples were pelleted by centrifugation (6,000×g) and resuspended in an equal volume of cold Hypho medium without succinate and supplemented with 100 mg/mL streptomycin to inhibit mCherry translation. Fixed cells were kept on ice prior to fluorescence measurements made using a BD LSR II Flow Cytometer. Flow cytometry data were then analyzed using the BioConductor flowCore package in R. Reported fluorescence values for flow cytometry are raw values from the BD LSR II and were not correlated to those of the Tecan Safire2.

Example 6

Harvesting of Biomass; Processing into Feed

Nutrient-rich biomass can be harvested via 1.) filtration, perhaps using a series of filters of decreasing pore size or tangential flow filtration 2.) continuous centrifugation, 3.) settling to the bottom of the fermentation vessel, or 4.) any combination of the above, or other approaches. Settling may be enhanced through the addition of a fining agent such as egg whites, gelatin, isinglass, the sequential addition of kieselsol and chitosan, carboxymethylcellulose, or other agents alone or in combination. Wet and dry cell mass can be determined before and after drying material in an oven. Total protein can be estimated via colorimetric assays (Bradford, M. M. *Analytical Biochemistry* (1976) 72: 248-254; Lowry, O. H. et al. *J. Biological Chemistry* (1951) 193: 265-275). Carotenoid content can be assessed spectrophotometrically following organic extraction (Takaichi and Shimada *Methods Enzymol*. (1992) 213: 374-385). Further characterization can occur via nuclear magnetic resonance or liquid chromatography-mass spectrometry (Holtin, K. et al. *Anal Bioanal Chem* (2009) 395: 1613-1622). Through comparison to standards, this can establish the identity and weight percentage of carotenoids present. Vitamins such as B-12 can be determined via bioassay (Berg, T. M. et al. *Appl. Environ. Microbiol*. (1976) 31: 459-464). Cellulose content can be determined enzymatically (Zhang, Y. H. et al. *Methods Mol. Biol*. (2009) 581: 213-231). Poly-β-hydroxybutyrate content can be determined by flow cytometry or spectorfluorometry (Degelau, A. et al. *Appl. Microbiol. Biotechnol*. (1995) 42: 653-657). Free amino acids can be quantified via derivativization and analysis via gas chromatography-mass spectrometry (Krömer, J. O. et al. *J. Bacteriol* (2004) 186: 1769-1784; Marx, C. J. et al. *PLoS Biology* (2005) 3: e16).

One method of preparing cell mass is via freeze-drying in a lyophilizer, and then readdition of dried cell powder into gel, pellet, or flake forms of fish food. Alternatively, fresh (wet) cell material may be added to other ingredients prior to preparation via drying or heating. In other methods, cell material may be disrupted via homogenization, sonication, enzymatic treatment, or other treatments alone or together in order to alter the bioavailability of pigments, other nutrients, and protein. This will likely be accompanied by addition of an antioxidant. The optimal method of preparation can be found by trial and error or by prediction based on the animal for which the feed is intended.

Trials to test the utility of pigmented methylotrophs as a carotenoid-rich protein source for aquaculture feed can proceed in various stages. As a simple first test of palatability, *Methylobacterium* can be added to a gel fish food at a smaller volume. Contingent upon interest in feeding, flavor additives such as fish hydrolysate can be adjusted, accordingly. As a second stage, the nutritional value of *Methylobacterium* cell material and the ability to deposit pigments can be assessed in a small, rapidly growing fish such as Amphiprion (i.e., clown fish). Using a combinatorial design, we can consider six initial treatments. Traditional fish food can be prepared with and without the addition of commercial astaxanthin. Pigment-free *Methylobacterium* and a high pigment strain (such as in Lee, M.-C. et al. *Evolution* (2009) 63: 2813-2830) can be added to varying levels, such as 5% and 25% total dry weight of feed, into 95% or 75% traditional feed. Further tests could compare additions to alternative technologies such as treated or untreated soy protein. From this we will be able to assess fish vigor, survival, weight gain and body dimensions, externally visible coloration in the scales, and pigment deposition in the flesh. Follow-up trials could assess the rate and specificity of deposition using isotopically-labelled biomass using $^{13}$C-methanol or $^{15}$N-ammonium. There are two grounds for determining the success of these trials. First, are the fish at least as healthy as the standard feed, or perhaps more healthy than a similar replacement with soy-based protein instead of *Methylobacterium*? Second, is there detectable pigmentation in the flesh and scales relative to the negative control, and how far toward (or above) the positive control is this coloration? Positive results in model organisms as indicators for larger, commercially relevant species will already indicate utility as a pigment-laden feed for ornamental fish, and may point to specific utility of sprilloxanthin if the coloration is distinct from that seen with astaxanthin. The ultimate effectiveness in aquaculture applications can be assessed with similar feeding trials performed with the commercial species to be utilized, such as salmon or shrimp. As above, among the important criteria are fish vigor, survival, weight gain, prevention of disease (e.g. enteritis), and body dimensions, externally visible coloration in the scales, and pigment deposition in the flesh.

Example 7

General Plasmid Construction

Deletion mutants were generated in *M. extorquens* PA1 using pPS004 (Michener et al, 2014. *J. Bacteriology*. 196: 2101-2107), a kanamycin-resistance allelic exchange vector derived from pCM433 (Marx 2008). Briefly, 500+ bp regions flanking the target locus were PCR amplified and assembled into pPS04 using Gibson isothermal assembly (Gibson 2009). All plasmids relevant to this study are listed in Table 1.

TABLE 1

List of relevant plasmids

| Plasmid | Description | Reference |
|---|---|---|
| pKB01 | deletion construct for ctrI-like locus (Mext_3011) | This work |
| pKB02 | deletion construct for crtF (Mext_2528) | This work |
| pKB03 | deletion construct for cluster of crtCDF (Mext_2725-26, -28) | This work |
| pCM433 | Allelic exchange vector | Marx 2008 |
| pPS04 | kanR derivative of pCM433 | Michener et al., 2014 |
| pRK2073 | helper plasmid for triparental matings | Figurski 1979 |

Construction of pKB01 to delete crtI-like locus (Mext_3011)

To delete Mext_3011 (a crtI-like gene), two flanking regions were amplified using the following oligonucleotide pairs: upstream, <u>ATGGATGCATATGCTGCAGCTCGAGCGGCCGCGGC</u>CCCCTTTGCCCTT (SEQ ID NO:27) plus <u>ATCCGGCACGGTTGACACTATGGCTGGGA</u> (SEQ ID NO:28); and downstream, <u>GCGCTGACGAAAATCCCAGCCATAGTGTCAACCGT</u>GCCGGATGCCCGT (SEQ ID NO:29) plus <u>GGTTAACACGCGTACGTAGGGCCCGCGGCCGCGG</u>GCGATGTTGGTGAA (SEQ ID NO:30). Underlined sequences denote overlapping regions designed to facilitate Gibson isothermal assembly. A map of the resulting plasmid—pKB01—is listed in FIG. 2.

Construction of pKB03 to delete crtCDF (Mext_2725-26, -28)

The construct to delete crtCDF (Mext_2725-26, -28) while maintaining crtE (Mext_2727) was slightly more complex, requiring 3 PCR products with the following primer pairs: upstream flank of crtCD, (SEQ ID NO: 31)
<u>ATGGATGCATATGCTGCAGCTCGAGCGGCCGC</u>CCGATTGCCTGCCCCTAG plus (SEQ ID NO: 32)
<u>GGATCAACGGTGATGCGAGGCGGAGCGCATTTTCGGTGGCAGGCGCCTGA</u>

GCGAAGTCC;

middle region encoding crtE (SEQ ID NO: 33)
CTGCCACCGAAAATG plus (SEQ ID NO: 34)
TTAGCGCCGCGGCAAGGCCGGTTCT;

and downstream flank of crtF, (SEQ ID NO: 35)
<u>CGAGCGATGGCGTGAGAACCGGCCTTGCC</u>GCGGCGCTAAGAGTGT plus (SEQ ID NO: 36)
<u>GGTTAACACGCGTACGTAGGGCCCGCGGCCGCC</u>GAATCGCCGCTGACA.

A map of the resulting plasmid—pKB03—is listed in FIG. 4.

Construction of pKB02 for ΔcrtF (Mext_2728)

A construct to delete crtF (Mext_2728) was inadvertently created during the Gibson assembly of pKB03 fragments. In this construct, approximately 129 bp of spurious PCR product (from Mext_1932) were assembled upstream of the middle and downstream fragments of pKB03 described above. Given that this upstream fragment bears no homology to the target locus, this region behaved as "vector" and was lost in the double-crossover recombinant, resulting in a clean deletion as verified by PCR analysis and Sanger sequencing.

Strain Construction

Deletion constructs were introduced into *M. extorquens* PA1 using triparental matings with the helper plasmid pRK2073 (Figurski 1979). Mutants were engineered in several *M. extorquens* PA1 genetic backgrounds: "wild-type" *M. extorquens* PA1 (Knief 2010); a Δcel mutant deficient in cellulose biosynthesis (Delaney 2013); and a double Δcel Δshc strain lacking both cellulose biosynthesis and squalene-hopane cyclase. Clean genomic deletions were confirmed by PCR analysis and Sanger sequencing using a combination of primers from the constructs, as well as the following oligonucleotides designed outside the region of recombination: pKB01, CTCCCCATCCTCGTGATC (SEQ ID NO:37) and GAGGAAGGCGTCCGGGTC (SEQ ID NO:38); pKB02, GTGCCGGATGCCCG (SEQ ID NO:39) T and CGCCGAAACCCGGATG (SEQ ID NO:40); pKB03, GCTCGCCACCAAGTTCG (SEQ ID NO:41) and CGCCGAAACCCGGATG (SEQ ID NO:42).

References Cited in This Example

Delaney N F, Kaczmarek M E, Ward L M, Swanson P K, Lee M-C, et al. (2013) Development of an optimized medium, strain and high-throughput culturing methods for *Methylobacterium extorquens*. PLoS ONE 8: e62957. doi: 10.1371/journal.pone.0062957.

Figurski D H, Helinski D R (1979) Replication of an origin-containing derivative of plasmid RK2 dependent on a plasmid function provided in trans. P Natl Acad Sci Usa 76: 1648-1652.

Gibson D G, Young L, Chuang R-Y, Venter J C, Hutchison C A, et al. (2009) Enzymatic assembly of DNA molecules up to several hundred kilobases. Nat Meth 6: 343-345. doi:10.1038/nmeth.1318.

Knief C, Frances L, Vorholt J A (2010) Competitiveness of diverse *Methylobacterium* strains in the phyllosphere of *Arabidopsis thaliana* and identification of representative models, including *M. extorquens* PA1. Microb Ecol 60: 440-452. doi:10.1007/s00248-010-9725-3.

Marx C J (2008) Development of a broad-host-range sacB-based vector for unmarked allelic exchange. BMC Research notes 1:1. doi:10.1186/1756-0500-1-1.

Example 8

Construction of CM3945

An allelic exchange plasmid was constructed from pCM433, a sacB-based suicide plasmid. The genomic region annotated as squalene hopene cyclase (shc) is numerically annotated in the reference *M. extorquens* PA1 genome as Mext_1944. To knockout the gene, PCR products of sequences upstream and downstream shc were ligated into pCM433 to create cloning vector pAB194.

The primer pair taccatggatgcatatgctgcagctcgagcCCG CGC CGC AGG AAT TC (SEQ ID NO:43) (forward) and CGC ATC GTT CTC GCC TCG TTC (SEQ ID NO:44) (reverse) was used to amplify the region upstream of the shc locus. The primer pair gag aca gtc gaa cga ggc gag aac gat gcg GCA ACC TGA AGC GGG GCA AC (SEQ ID NO:45) (forward) and ggttaacacgcgtacgtagggcccgcggccGAT TGA GAC CCG CGG GTC ATC (SEQ ID NO:46) (reverse) was used to amplify the region downstream of the she locus. These primers were designed to add homology to the pCM433 backbone.

Following digestion of pCM433 with NotI, the upstream and downstream PCR products were ligated into the vector backbone via Gibson assembly, generating cloning vector pAB194.

CM3945 was generated by mating pAB194 into the recipient strain *M. extorquens* PA1 cel deletion strain (CM2730; Delaney et al., 2013). The allelic exchange was performed as described in Marx et al 2008. The deletion was confirmed by Sanger sequencing.

Example 9

Grunt Trial

An experiment was designed for growing the smallmouth grunt (*Haemulon chrysargyreum*) on four different experimental diets to determine if KnipBio's SCP, or KBM, was a suitable feed ingredient for a model fish. The four diets were composed of (1) a standard commercially available grunt diet, (2) the standard diet plus astaxanthin pigment (~80 PPM), (3) a diet containing 5% of the total feed pellet replaced by KnipBio single cell protein (KBM), and (4) a diet with 25% of the fish meal replaced by KBM (~60 PPM carotenoids). CM3945 strain was used to produce KBM. Fish length, weight, feed conversion ratio, and gut microbiota were all assessed. Each condition was tested in triplicate (12 aquarium tanks) with approximately 15 fish in each tank, for a total of 180 fish.

FIG. 5 shows growth of the smallmouth grunt using 4 experimental diets including a 25% inclusion of KBM In this pilot trial, smallmouth grunts were fed to satiation over the course of 34 days using the four experimental diets. The data suggests that the two diets with carotenoids (at roughly similar PPM levels), support the highest growth rates relative to the control diets without pigments over the same time (see FIG. 12). Growth of the grunt was observed to be 370% and 391% for the Control+Pigment and the 25% KBM inclusion respectively. The averaged-out feed conversion ratio (FCR) ranged from 1.09-1.24.

An interesting indication from this data is that the pigments in KBM appear to be bio-accessible to the fish tested which implies the intense processing for pigment extraction typical with algae and yeast today is unnecessary in this system. Advantages to this include lower processing costs as well as longer viability of the anti-oxidant pigments as exposure to O2-damage is considerably lower while remaining intact.

In part, KnipBio's single cell protein (KBM) serves as a viable protein alternative for animal feeds given its natural composition and potential for enhanced expression. In aquaculture and agriculture, vegetable proteins (e.g., soy) are commonly used. However, these vegetable protein sources lack essential amino acids like lysine, methionine and others which require formulated feeds to add these essential nutrients exogenously. As seen in FIG. 6, KBM as a raw ingredient is largely comparable to commercially available final feeds based on soy or fish meal. The genetic tractability of *M. extorquens* lends itself to the further fine tuning of specific or groups of amino acids. Another consideration for the use of vegetable proteins are the carbohydrates that are often associated as high as 10%. Certain animals (e.g., salmon) react unfavorably to excess sugar and result in stomach inflammation (enteritis). KBM carbohydrate composition can be an order of magnitude lower minimizing or avoiding these effects considerably. Blood meal and poultry byproducts are often included as part or in combination with our proteins for animal feeds. One of the significant drawbacks to this material is the undigested phosphorous content from bone that then subsequently enters the environment. The composition of KBM is 5-10× lower in phosphorous which means more of the feed is usable to the animal simultaneously resulting in a lower environmental footprint.

The invention claimed is:

1. A biomass comprising substantially one or more isolated methylotrophic bacterial cultures,
   wherein the bacteria are genetically modified to produce elevated levels of a carotenoid compound relative to the corresponding unmodified bacterium;
   wherein the bacterium of the cultures is selected from the group consisting of *Methylomonas, Methylobacter, Methylosinus, Methylocyctis, Methylomicrobium, Methylophilus, Methylobacterium, Hyphomicrobium, Bacillus, Nocardia, Arthrobacter, Rhodopseudomonas,* and *Pseudomonas*; and
   wherein the genetically modified bacterium is modified so that one or more genes producing enzymes that divert isoprenoid compounds from the carotenoid biosynthetic pathway are blocked or deleted.

2. The biomass of claim 1, wherein the biomass is in a dry or substantially dry form.

3. The biomass of claim 1, wherein the bacterium is a *Methylobacterium*.

4. The biomass of claim 3, wherein the bacterium is *M. extorquens*.

5. The biomass of claim 4, wherein the strain of *M. extorquens* is selected from the group consisting of *M. extorquens* AM1, *M. extorquens* DM4, *M. extorquens* CM4, *M. extorquens* PA 1, *M. extorquens* BJ001 (formerly *M. populi*), *M. radiotolerans, M. nodulans,* and *Methylobacterium* spp. 4-46.

6. The biomass of claim 1, wherein the carotenoid compound is selected from the group consisting of β-carotene, lycopene, rhodopin, astaxanthin and spirilloxanthin.

7. The biomass of claim 1, wherein the bacterium comprises a non-lethal knock-out of shc.

8. A feed composition, comprising the biomass of claim 1.

9. The feed composition of claim 8, wherein the biomass is obtained without bacterial lysis.

10. The feed composition of claim 9, wherein the biomass is collected by filtering, sedimentation, or centrifugation.

11. The feed composition of claim 8, wherein the composition contains at least 1% of the biomass by weight.

12. The feed composition of claim 8, wherein the composition is optimized for consumption by fish.

13. The feed composition of claim 12, wherein the fish comprises a species farmed for human consumption that has pink-, reddish-, yellow-, or orange-colored flesh.

14. The feed composition of claim 12, wherein the composition comprises one or more of: EPA, DHA, taurine, and an essential amino acid.

15. A method of preparing a biomass, the method comprising:
   (a) culturing in an appropriate medium the genetically modified bacteria of claim 1, and
   (b) collecting the biomass.

16. The feed composition of claim 13, wherein the biomass is collected by filtering, sedimentation, or centrifugation.

17. The biomass of claim 4, wherein the bacterium is *M. extorquens* comprising a non-lethal knock-out of shc.

18. A method of producing fish or seafood, the method comprising:
   (a) farming fish or seafood, and
   (b) providing the feed composition of claim 8 to the fish or seafood.

19. The biomass of claim 1, wherein the genetically modified bacterium does not comprise heterologous nucleic acid sequences that encode an enzyme of a carotenoid biosynthetic pathway.

20. The biomass of claim 1, wherein the genetic modification consists of blocking or deleting one or more genes producing enzymes that divert isoprenoid compounds from the carotenoid biosynthetic pathway.

21. The biomass of claim 1, wherein the genetically modified bacterium is modified by blocking or deleting one or more of the genes hpnC, hpnD, hpnE, shc (hpnF), bchG, bchP, crtC, crtD, and crtF.

22. The biomass of claim 1, wherein the genetically modified bacterium is modified by blocking or deleting one or more of the genes hpnC, hpnD, hpnE and shc (hpnF).

* * * * *